United States Patent
Bradbury et al.

(10) Patent No.: US 10,766,905 B2
(45) Date of Patent: *Sep. 8, 2020

(54) [1,2,4]TRIAZOLO[4,3-B]PYRIDAZINES FOR USE IN THE TREATMENT OF PROLIFERATIVE DISEASES

(71) Applicant: AstraZeneca AB, Sodertalje (SE)

(72) Inventors: Robert Hugh Bradbury, Cheshire (GB); Alfred Arthur Rabow, Cheshire (GB); Michael James Waring, Cheshire (GB); James Francis McCabe, Cheshire (GB); Steven Christopher Glossop, Cheshire (GB); Arshed Mahmood, Cheshire (GB); Zoe Ann Cotter, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/528,738

(22) Filed: Aug. 1, 2019

(65) Prior Publication Data
US 2020/0055861 A1 Feb. 20, 2020

Related U.S. Application Data

(63) Continuation of application No. 15/950,443, filed on Apr. 11, 2018, now Pat. No. 10,407,432, which is a continuation of application No. 15/329,274, filed as application No. PCT/GB2015/052143 on Jul. 24, 2015, now Pat. No. 9,944,650.

(60) Provisional application No. 62/029,676, filed on Jul. 28, 2014.

(51) Int. Cl.
C07D 487/04 (2006.01)
A61P 35/00 (2006.01)
E21B 7/06 (2006.01)

(52) U.S. Cl.
CPC .............. *C07D 487/04* (2013.01); *E21B 7/06* (2013.01); *E21B 7/062* (2013.01); *C07B 2200/13* (2013.01)

(58) Field of Classification Search
CPC .................................................. C07D 487/04
See application file for complete search history.

(56) References Cited

U.S. PATENT DOCUMENTS

| | | | | |
|---|---|---|---|---|
| 8,258,140 B2 * | 9/2012 | Bradbury | ............ | A61K 31/5025 514/255.01 |
| 9,944,650 B2 * | 4/2018 | Bradbury | ................ | E21B 7/062 |
| 10,407,432 B2 * | 9/2019 | Bradbury | ................ | E21B 7/06 |
| 2010/0292222 A1 * | 11/2010 | Bradbury | ............. | C07D 487/04 514/218 |
| 2014/0135336 A1 | 5/2014 | Engelhardt | | |

FOREIGN PATENT DOCUMENTS

| | | |
|---|---|---|
| WO | 2007065664 A2 | 6/2007 |
| WO | 2009081197 A1 | 7/2009 |
| WO | 2010092371 A1 | 8/2010 |
| WO | 2010131022 A1 | 11/2010 |
| WO | 2011054553 A1 | 5/2011 |

OTHER PUBLICATIONS

Cancer Drug Design and Discovery, Neidle, Stephen, ed. (Elsevier/Academic Press), pp. 427-431 {2008}. (Year: 2008).*
Wadhwa, et al., Cureus, "Bromodomain Inhibitor Review: Bromodomain and Extra-terminal Family Protein Inhibitors as a Potential New Therapy in Central Nervous System Tumors", May 2016; 8(5}; e620, pp. 1-8 (Year: 2016).*
Bradbury Robert H et al: "Discovery of AZD3514, a small-molecule androgen receptor downregulator for treatment of advanced prostate cancer", Bioorganic & Medicinal Chemistry Letters, Pergamon, Amsterdam, NL, vol. 23, No. 7, Feb. 21, 2013 (Feb. 21, 2013), pp. 1945-1948.
Jadav Pradip et al: "Design, synthesis and biological evaluation of novel aminomethyl-piperidones based DPP-IV Inhibitors", Bioorganic & Medicinal Chemistry Letters, vol. 24, No. 8, Mar. 12, 2014 (Mar. 12, 2013), pp. 1918-1922.
Cancer Drug Design and Discovery, Neidle, Stephen, ed. (Elsevier/Academic Press), pp. 427-431 (2008).
Wadhwa, et al., Cureus, "Bromodomain Inhibitor Review: Bromodomain and Extra-terminal Family Protein Inhibitors as a Potential New Therapy in Central Nervous System Tumors", May 2016; 8(5); e620, pp. 1-8.

* cited by examiner

*Primary Examiner* — Emily A Bernhardt

(57) ABSTRACT

The invention concerns compounds of Formula (I)

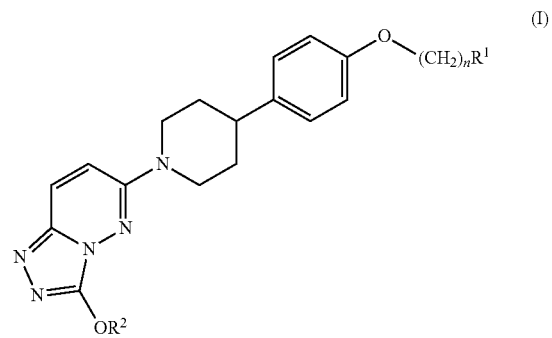

or pharmaceutically-acceptable salts thereof, wherein $R^1$, $R^2$ and n have any of the meanings defined hereinbefore in the description; processes for their preparation, pharmaceutical compositions containing them and their use as anti-proliferative and/or cell-killing agents.

8 Claims, 14 Drawing Sheets

Figure 1: X-Ray Powder Diffraction Pattern of Compound A, Form A

Figure 2: DSC Thermogram Compound A, Form A

Figure 3: X-Ray Powder Diffraction Pattern of

Compound A:6-hydroxy-2-naphthoic acid
(1:1) co-crystal, Form A

Figure 4: DSC Thermogram of

Compound A:6-hydroxy-2-naphthoic acid
(1:1) co-crystal, Form A

Figure 5: Plot of Tumour Volume versus Time

Figure 6: Stacked plot of $^{13}C$ ss NMR spectra (bottom spectra :Compound A:6-hydroxy-2-naphthoic acid (1:1)co-crystal, Form A
middle spectra: Compound A (free base)
top spectra: 6 hydroxy-2-naphthoic acid)

Figure 7: Stacked plot of $^{15}$N ssNMR spectra of

Compound A:6 hydroxy-2-naphthoic acid (1:1) co-crystal, Form A (bottom spectra – contact time 2 ms)
(top spectra – contact time 200 μs)

¹H NMR spectra of Compound A:6 hydroxy-2-naphthoic acid (1:1) co-crystal, Form A

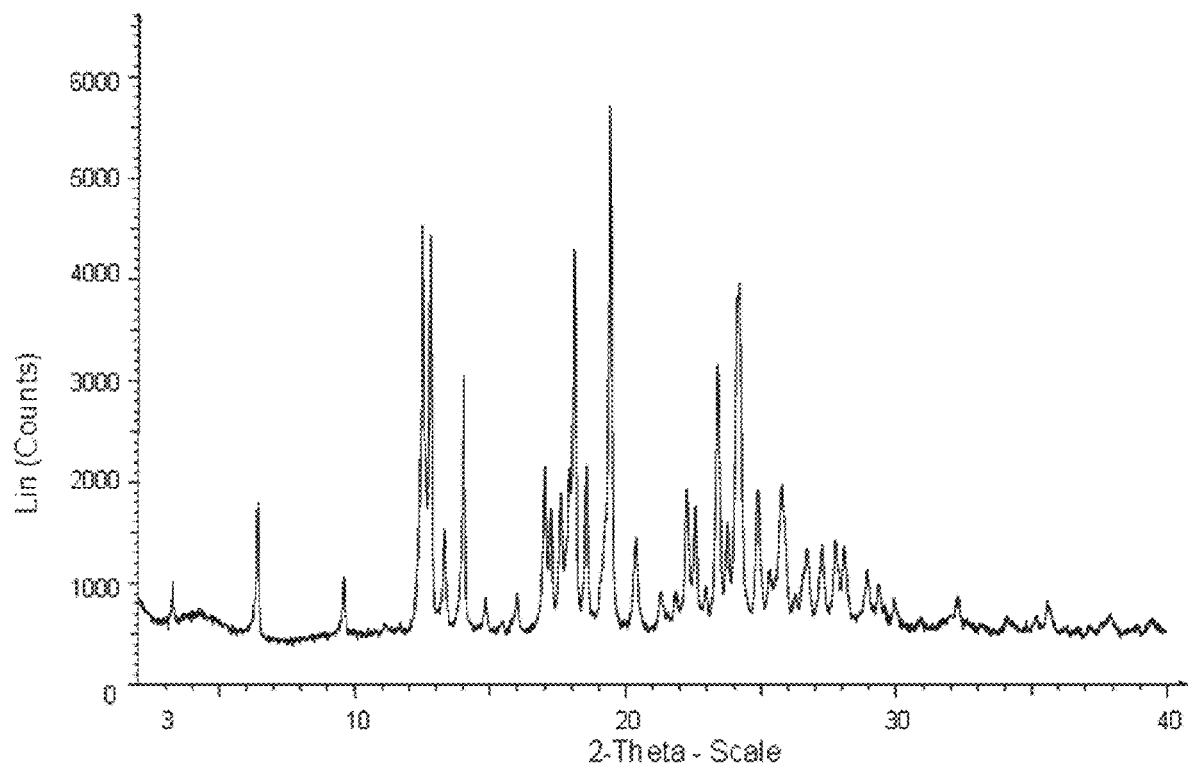
Figure 9: X-Ray Powder Diffraction Pattern of Compound A:6-hydroxy-2-naphthoic acid (1:1) co-crystal, Form A

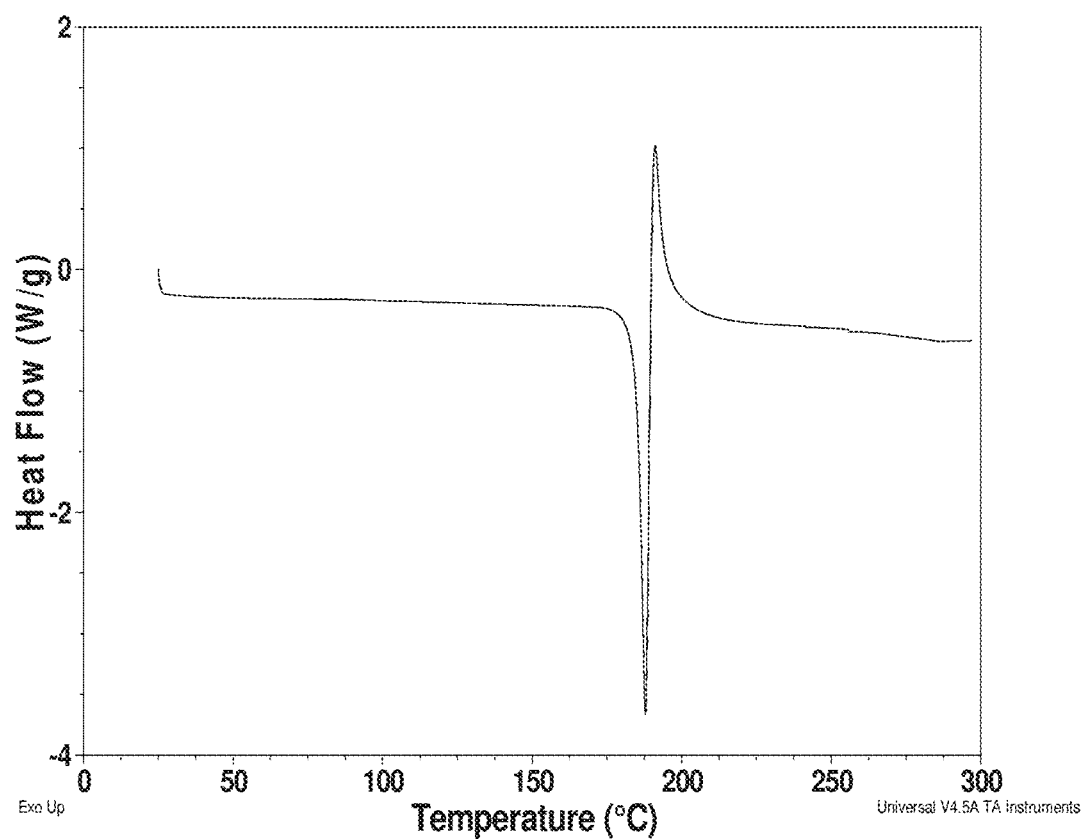
Figure 10: DSC Thermogram of Compound A:6-hydroxy-2-naphthoic acid (1:1) co-crystal, Form A

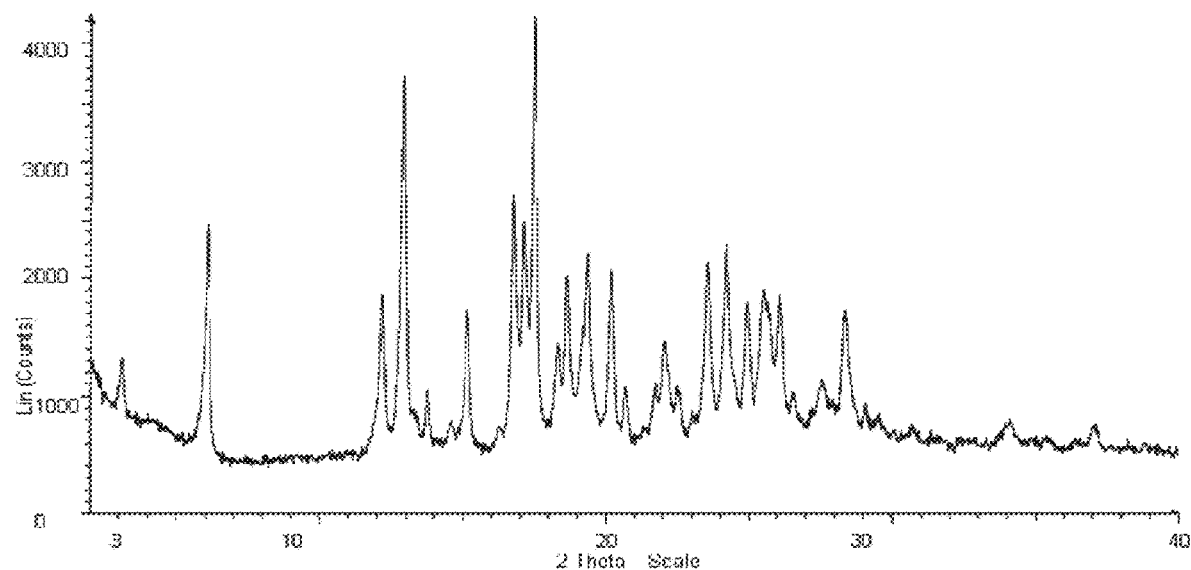
Figure 11: X-Ray Powder Diffraction Pattern of Compound A:
6-hydroxy-2-naphthoic acid (1:1) co-crystal, Form B

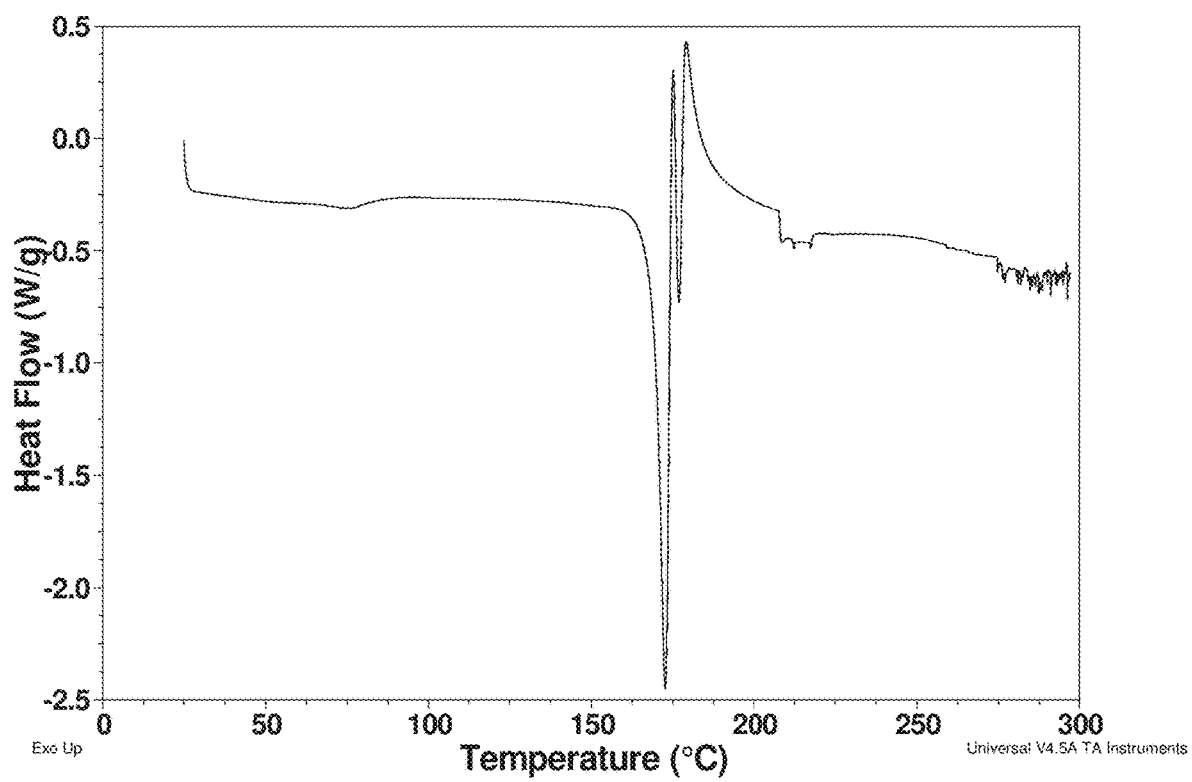
Figure 12: DSC Thermogram of Compound A: 6-hydroxy-2-napthoic acid (1:1) co-crystal, Form B

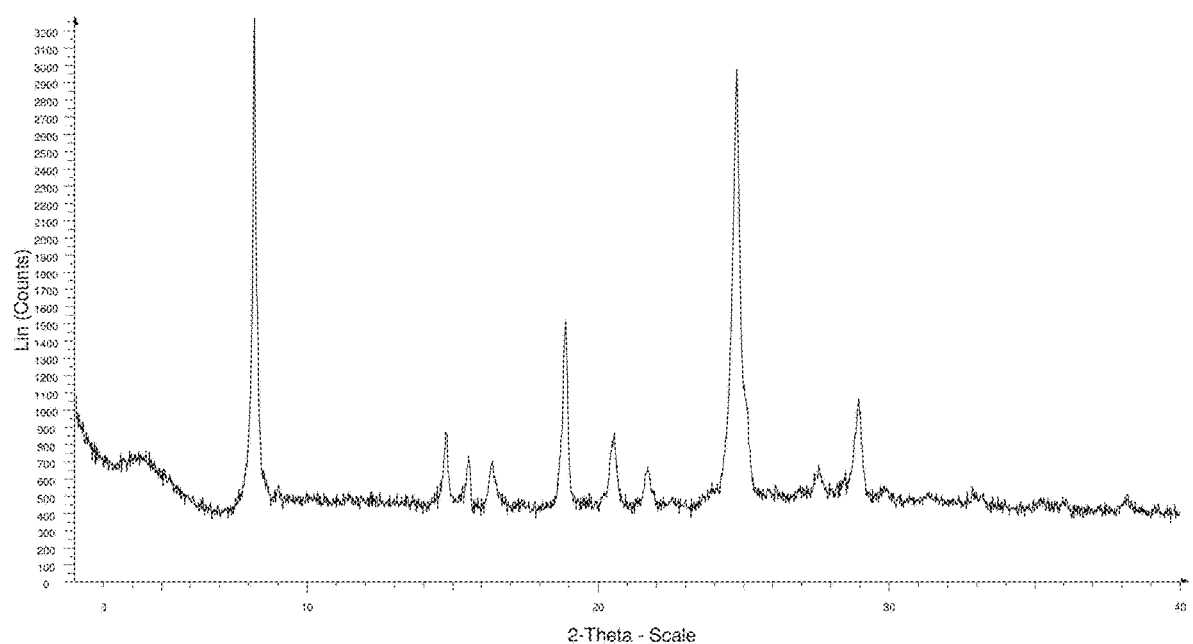
Figure 13: X-Ray Powder Diffraction Pattern of Compound A: 6-hydroxy-2-naphoic acid (1:1) co-crystal, Form C

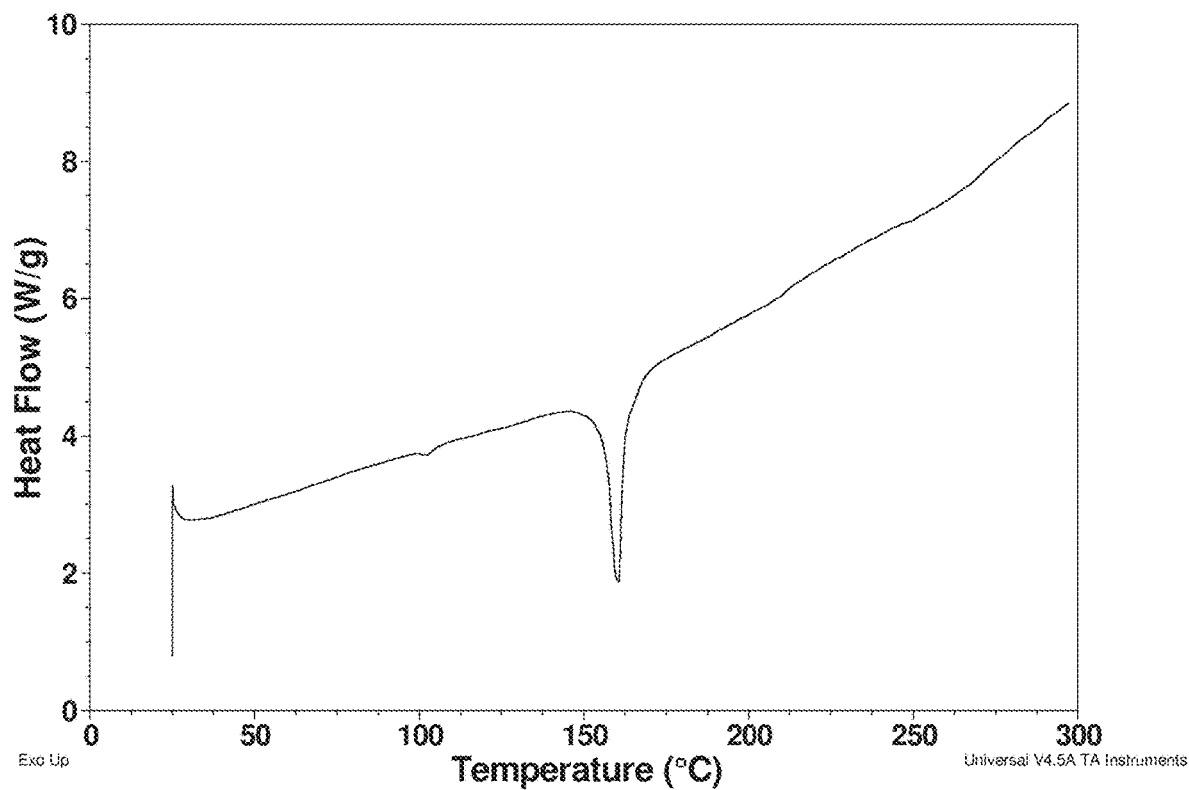
Figure 14: DSC Thermogram of Compound A: 6-hydroxy-2-naphoic acid (1:1) cocrystal, Form C

[1,2,4]TRIAZOLO[4,3-B]PYRIDAZINES FOR USE IN THE TREATMENT OF PROLIFERATIVE DISEASES

CROSS-REFERENCE TO RELATED APPLICATIONS

This application is a continuation of U.S. Pat. No. 10,407,432, issued on Sep. 10, 2019, which is a continuation of U.S. Pat. No. 9,944,650, issued on Apr. 17, 2018, which is a U.S. National Stage application of International Application No. PCT/GB2015/052143, filed on Jul. 24, 2015, which claims the benefit under 35 U.S.C. § 119(e) of U.S. Provisional Patent Application No. 62/029,676, filed on Jul. 28, 2014, each of which is incorporated by reference.

This application is a continuation of U.S. application Ser. No. 15/950,443, filed on Apr. 11, 2018, which is, in turn, a continuation of U.S. application Ser. No. 15/329,274, filed on Jan. 26, 2017, which is a U.S. National Stage application of International Application No. PCT/GB2015/052143, filed on Jul. 24, 2015, which claims the benefit under 35 U.S.C. § 119(e) of U.S. Provisional Patent Application No. 62/029,676, filed on Jul. 28, 2014, each of which is incorporated by reference.

The invention concerns certain substituted triazolopyridazine (TPDZ) compounds or pharmaceutically acceptable salts thereof, which possess anti-cancer activity and are accordingly useful in methods of treatment of the human or animal body. The invention also concerns a process for the manufacture of said TPDZ compounds, pharmaceutical compositions comprising said compounds or pharmaceutically acceptable salts thereof, and to methods of treatment of cancers in warm-blooded animals such as man.

The invention also relates to TPDZ compounds that are inhibitors of one or more bromodomain-containing proteins, in particular the BET family of bromodomain-containing proteins.

Bromodomain-containing proteins are implicated in diverse diseases and are of substantial interest as therapeutic targets. The bromodomain is a highly conserved structural fold that recognizes acetylated-lysine residues and is found in large multidomain proteins associated with chromatin remodeling transcription control, methyl or acetyltransferase activity or helicases. The BET family of bromodomain containing proteins is comprised of four members (BRD2, BRD3, BRD4, and BRDt) which all display a common domain architecture of N-terminal tandem bromodomains capable of binding to acetylated lysine residues in histones and transcription factors. BRD4 plays an important role in gene transcriptional regulation as evidenced by its association with the positive transcription elongation factor b (pTEFb) (Jang et al. Mol. Cell, 2005, 19, 523-534), general transcription cofactor Mediator (Chiang, F1000 Biol. Rep, 2009, 1, 98), gene-specific pro-inflammatory factor NFkB (Huang et al. Mol. Cell Biol. 2009, 29, 1375-1387) and virus-encoded transcriptional regulators (You et al. Cell, 2004, 117, 349-360). It is observed that BRD4 has asymmetrical loading at extra large enhancers that are associated with a small subset of genes which often constitute the oncogenic and lineage-specific transcriptional programs in a particular cellular context (Loven et al. Cell, 2013, 153, 320-334). Similarly, BRD2 and BRD3 are reported as transcription regulators binding to hyper-acetylated chromatin regions of growth promoting genes (LeRoy et al. Mol. Cell. 2008, 30, 51-60). It has also been reported that BRD4 or BRD3 may fuse with NUT (nuclear protein in testis) forming novel oncogenes, BRD4-NUT or BRD3-NUT, in a highly malignant form of epithelial neoplasia (French et al. Cancer Research, 2003, 63, 304-307 and French et al. Journal Clinical Oncology, 2004, 22, 4135-4139). Data suggests that BRD-NUT fusion proteins contribute to carcinogenesis (French et al. 2008, Oncogene, 27, 2237-2242).). It is also found that BRD4 gene is altered in the form of gene amplification in serous ovarian and other cancers in The Cancer Genome Atlas (TCGA) dataset. All BET family members have been reported to have some function controlling or executing aspects of the cell cycle and have been shown to remain in complex with chromosomes during cell division, suggesting a role in the maintenance of epigenetic memory. Not surprisingly, BET family members were recently established as being important for the maintenance of many tumor types for example, acute myeloid and mixed lineage leukemia (AML), multiple myeloma (MM), lymphoma, glioblastoma and neuroblastoma. BRD4 inhibition potently suppresses Myc, ER, BCl2, and other oncogenes which are frequently altered in cancer. Modulation of these key genes is believed to contribute to the anti-tumor phenotype of BET inhibition In addition, BET inhibitors have been shown to have anti-inflammatory properties (Nicodeme et al. Nature, 2010, 468, 1119-1123) and reactivate latent HIV transcription in cell line models of latency (Banerjee et al. J Leukoc Biol, 2012, 92, 1147-1154).

Recently, a few compounds have been reported as bromodomain inhibitors, for example benzodiazepines derivatives such as those disclosed in WO2011/054553. However, there remains a need for developing novel and potent bromodomain inhibitors that can be used to treat diseases and indications where bromodomain containing proteins are implicated.

The compounds of the invention have been found to possess activity as inhibitors of bromodomain-containing proteins, such as the BET family of bromodomains, for example BRD4, BRD2, BRD3 and BRDt, and the tandom domains thereof, for example BRD4(1) and BRD4(2).

According to one aspect of the invention there is provided a compound of Formula (I) or a pharmaceutically acceptable salt thereof

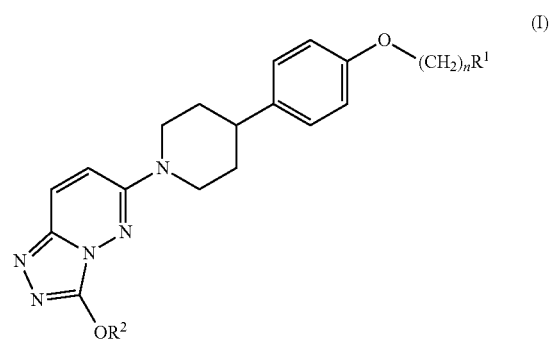

wherein: —

R$^1$ is the group

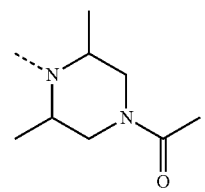

or the group

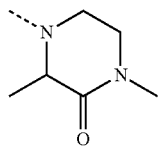

and ---- denotes the point of attachment;
R² is a $C_1$-$C_4$alkyl; and
n is 2 or 3.

In another aspect of the invention, there is provided a compound of Formula (I) as defined above.

In a further aspect of the invention R² is methyl.

In yet a further aspect of the invention, R¹ is the group

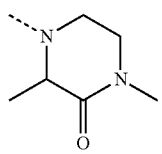

R² is $C_1$-$C_4$ alkyl; and
n is 2.

In one aspect of the invention, the compound of Formula (I) is a compound selected from:
4-(2-(4-(1-(3-methoxy-[1,2,4]triazolo[4,3-b]pyridazin-6-yl)piperidin-4-yl)phenoxy)ethyl)-1,3-dimethylpiperazin-2-one;
1-(4-(2-(4-(1-(3-methoxy-[1,2,4]triazolo[4,3-b]pyridazin-6-yl)piperidin-4-yl)phenoxy)ethyl)-3,5-dimethylpiperazin-1-yl)ethanone;
4-(3-(4-(1-(3-methoxy-[1,2,4]triazolo[4,3-b]pyridazin-6-yl)piperidin-4-yl)phenoxy)propyl)-1,3-dimethylpiperazin-2-one; and
1-(4-(3-(4-(1-(3-methoxy-[1,2,4]triazolo[4,3-b]pyridazin-6-yl)piperidin-4-yl)phenoxy)propyl)-3,5-dimethylpiperazin-1-yl)ethanone.

In another aspect of the invention, the compound of Formula (I) is a compound of Formula (IA):

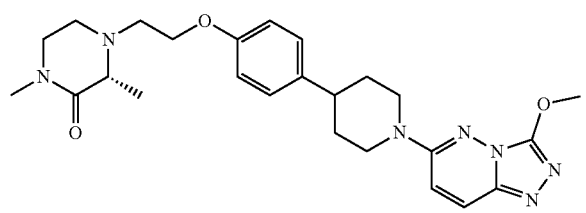

(IA)

The compound of Formula (IA) is also referred to hereinafter as Compound A.

In another aspect, the compound of Formula (I) is a compound of Formula (IB):

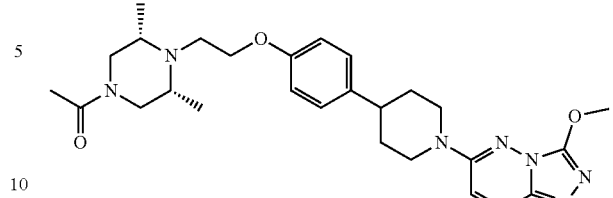

(IB)

According to a further aspect of the invention, the compound of Formula (I) is a compound of Formula (IC):

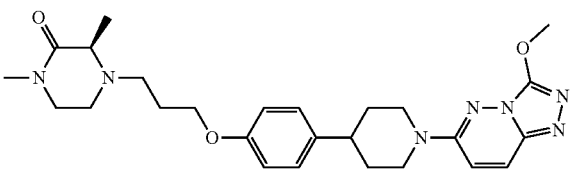

(IC)

According to a further aspect of the invention, the compound of Formula (I) is a compound of Formula (ID):

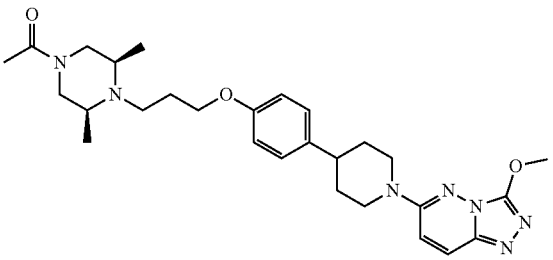

(ID)

A further aspect provides any of the aspects defined herein (for example the aspect of claim 1) with the proviso that one or more specific Examples (for instance one, two or three specific Examples) selected from the group consisting of Examples 1, 2, 3 and, 4, is individually disclaimed.

BRIEF DESCRIPTION OF THE DRAWINGS

FIG. 9: X-Ray Powder Diffraction Pattern of Compound A:6-hydroxy-2-naphthoic acid (1:1) co-crystal, Form A.

FIG. 10: DSC Thermogram of Compound A:6-hydroxy-2-naphthoic acid (1:1) co-crystal, Form A.

FIG. 11: X-Ray Powder Diffraction Pattern of Compound A:6-hydroxy-2-naphthoic acid (1:1) co-crystal, Form B.

FIG. 12: DSC Thermogram of Compound A:6-hydroxy-2-naphthoic acid (1:1) co-crystal, Form B.

FIG. 13: X-Ray Powder Diffraction Pattern of Compound A:6-hydroxy-2-naphthoic acid (1:1) co-crystal, Form C.

FIG. 14: DSC Thermogram of Compound A:6-hydroxy-2-naphthoic acid (1:1) co-crystal, Form C.

Some of the compounds of Formula (I) may be crystalline and may have more than one crystalline form. It is to be understood that the invention encompasses any crystalline or amorphous form, or mixtures thereof, which form possess properties useful in BET inhibitory activity and, such as, BRD2, BRD3, BRD4, and BRDt inhibitory activity. It is well known how to determine the efficacy of a crystalline or amorphous form by the standard tests described hereinafter.

It is generally known that crystalline materials may be analysed using conventional techniques such as, for example, X-ray powder diffraction (hereinafter XRPD) analysis and Differential Scanning calorimetry (hereinafter DSC).

As an example, the compound of Example 1 exhibits crystallinity and one crystalline form, Form A, has been identified.

Accordingly, a further aspect of the invention is Form A of Compound A (Example 1).

According to the invention, there is provided a crystalline form, Form A, of Compound A which has a XRPD pattern with at least one specific peak at about 2-theta=20.9°, measured using CuKα radiation.

According to the invention there is provided a crystalline form, Form A, of Compound A which has a XRPD pattern with at least one specific peak at about 2-theta=16.7°, measured using CuKα radiation.

According to the invention there is provided a crystalline form, Form A, of Compound A which has a XRPD pattern with at least two specific peaks at about 2-theta=20.9° and 16.7°, measured using CuKα radiation.

According to the invention there is provided a crystalline form, Form A, of Compound A which has a XRPD pattern with specific peaks at about 2-theta=20.9, 16.7, 20.2, 21.2, 27.4, 18.0, 16.8, 23.6, 15.1 and 15.5°, measured using CuKα radiation.

Figure 1:
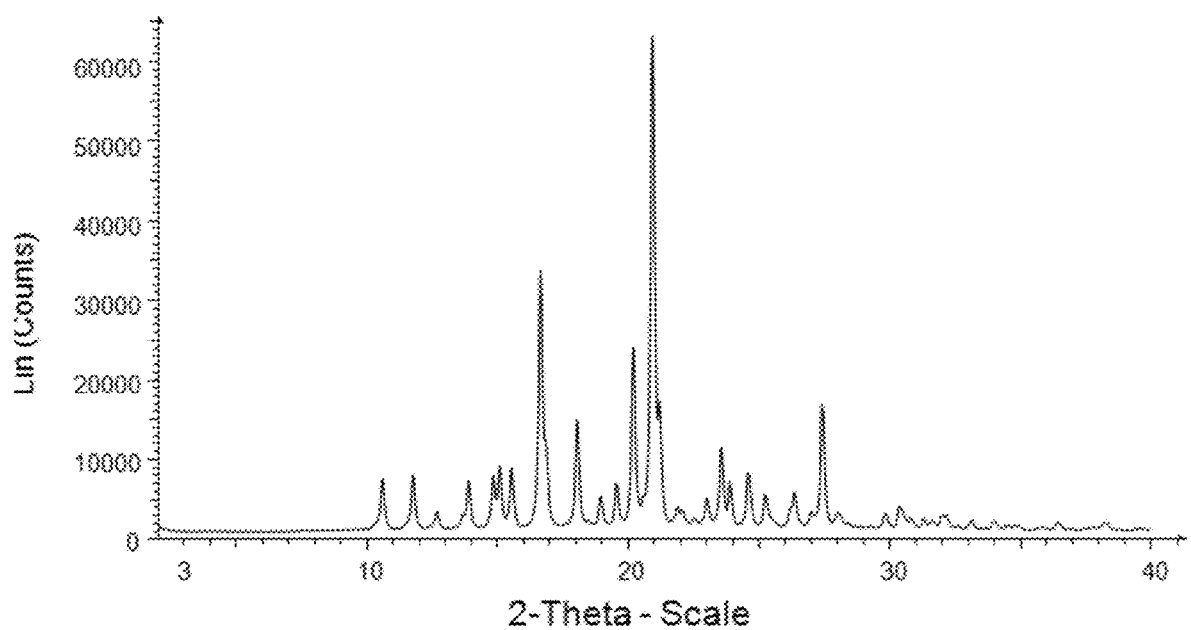
FIG. 1: X-Ray Powder Diffraction Pattern of Compound A, Form A.

According to the invention there is provided a crystalline form, Form A, of Compound A which has a XRPD pattern substantially the same as the XRPD shown in FIG. 1, measured using CuKα radiation.

According to a further aspect of the invention, there is provided a crystalline form, Form A, of Compound A which has a XRPD pattern with at least one specific peak at 2-theta=20.9° plus or minus 0.2° 2-theta, measured using CuKα radiation.

According to the invention there is provided a crystalline form, Form A, of Compound A which has a XRPD pattern with at least one specific peak at 2-theta=16.7° plus or minus 0.2° 2-theta, measured using CuKα radiation.

According to the invention there is provided a crystalline form, Form A, of Compound A which has a XRPD pattern with at least two specific peaks at 2-theta=20.9° and 16.7° plus or minus 0.2° 2-theta, measured using CuKα radiation.

According to the invention there is provided a crystalline form, Form A, of Compound A which has a X-ray powder diffraction pattern with specific peaks at 2-theta=20.9, 16.7, 20.2, 21.2, 27.4, 18.0, 16.8, 23.6, 15.1 and 15.5° plus or minus 0.2° 2-theta, measured using CuKα radiation.

When it is stated that the invention relates to a crystalline form of Compound A, Form A, the degree of crystallinity is conveniently greater than about 60%, more conveniently greater than about 80%, preferably greater than about 90% and more preferably greater than about 95%. Most preferably the degree of crystallinity is greater than about 98%.

Some of the compounds of Formula (I) may form co-crystals with specific co-former molecules. It is to be understood that the present invention encompasses any such co-crystals, which possess properties useful in BET inhibitory activity and, such as, BRD2, BRD3, BRD4, and BRDt inhibitory activity It is well known how to determine the efficacy of such co-crystals by the standard tests described hereinafter.

Accordingly, the invention provides a co-crystal of a compound of Formula (I) and a co-former molecule.

Accordingly, to a further aspect of the invention there is provided a co-crystal of Compound A and the co-former molecule 6-hydroxy-2-naphthoic acid.

For the avoidance of doubt, the term "co-crystal" refers to a multicomponent system in which there exists a host API (active pharmaceutical ingredient) molecule or molecules and a guest (or co-former) molecule or molecules in the same crystal lattice. In a co-crystal, both the API molecule and the guest (or co-former) molecule exist as solids at room temperature when alone in their pure form (in order to distinguish the co-crystal from solvates or hydrates). In a co-crystal the API and co-former molecules interact by hydrogen bonding and possibly other non-covalent interactions.

In preparing co-crystals of Compound A with 6-hydroxy-2-naphthoic acid, where Compound A is the API, a range of API:co-former molar ratios/stoichiometries may be achieved, for example an overall API:co-former molar ratio of 1:1, although this may vary slightly, depending, for example, on the characterisation measurements. Accordingly, the invention provides a co-crystal of Compound A and co-former molecule 6-hydroxy-2-naphthoic acid with a molar ratio of Compound A:6-hydroxy-2-naphthoic acid in the range 1:0.8 to 1:1.2. In one aspect of the invention there is provided a Compound A:6-hydroxy-2-naphthoic acid (1:1) co-crystal.

In a further aspect of the invention the co-crystal of Compound A with 6-hydroxy-2-naphthoic acid is in a crystalline form, Form A.

According to the invention there is provided a crystalline form, Form A, of Compound A:6-hydroxy-2-naphthoic acid (1:1) co-crystal.

According to the invention there is provided a crystalline form, Form A, of Compound A:6-hydroxy-2-naphthoic acid (1:1) co-crystal which has a XRPD pattern with at least one specific peak at about 2-theta=19.4°, measured using CuKα radiation.

According to the invention there is provided a crystalline form, Form A, of Compound A:6-hydroxy-2-naphthoic acid (1:1) co-crystal, which has a XRPD pattern with at least one specific peak at about 2-theta=12.5°, measured using CuKα radiation.

According to the invention there is provided a crystalline form, Form A, of Compound A:6-hydroxy-2-naphthoic acid (1:1) co-crystal which has a XRPD pattern with at least two specific peaks at about 2-theta=19.4° and 12.5°, measured using CuKα radiation.

According to the invention there is provided a crystalline form, Form A, of Compound A:6-hydroxy-2-naphthoic acid (1:1) co-crystal which has a XRPD pattern with specific peaks at about 2-theta=19.4, 12.5, 12.8, 18.1, 24.2, 23.4, 14.0, 18.6, 17.0, and 17.9°, measured using CuKα radiation.

According to the invention there is provided a crystalline form, Form A, of Compound A:6-hydroxy-2-naphthoic acid (1:1) co-crystal which has a XRPD pattern substantially the same as the XRPD pattern shown in FIG. 9, measured using CuKα radiation.

According to the invention there is provided a crystalline form, Form A, of Compound A:6-hydroxy-2-naphthoic acid (1:1) co-crystal which has a XRPD pattern with at least one specific peak at 2-theta=19.4° plus or minus 0.2° 2-theta, measured using CuKα radiation.

According to the invention there is provided a crystalline form, Form A, of Compound A:6-hydroxy-2-naphthoic acid (1:1) co-crystal which has a XRPD pattern, with at least one specific peak at 2-theta=12.5° plus or minus 0.2° 2-theta, measured using CuKα radiation.

According to the present invention there is provided a crystalline form, Form A, of Compound A:6-hydroxy-2-naphthoic acid (1:1) co-crystal which has a XRPD pattern, with at least two specific peaks at 2-theta=19.4° and 12.5° wherein said values may be plus or minus 0.2° 2-theta, measured using CuKα radiation.

According to the invention there is provided a crystalline form, Form A, of Compound A:6-hydroxy-2-naphthoic acid (1:1) co-crystal which has a XRPD pattern with specific peaks at 2-theta=19.4, 12.5, 12.8, 18.1, 24.2, 23.4, 14.0, 18.6, 17.0 and 17.9° wherein said values may be plus or minus 0.2° 2-theta, measured using CuKα radiation.

In a further aspect of the invention the co-crystal of Compound A with 6-hydroxy-2-naphthoic acid is in a crystalline form, Form B. According to the invention there is provided a crystalline form, Form B, of Compound A:6-hydroxy-2-naphthoic acid (1:1) co-crystal.

According to the invention there is provided a crystalline form, Form B, of Compound A: 6-hydroxy-2-naphthoic acid (1:1) co-crystal which has a XRPD pattern with at least one specific peak at about 2-theta=15.2° measured using CuKα radiation.

According to the invention there is provided a crystalline form, Form B, of Compound A: 6-hydroxy-2-naphthoic acid (1:1) co-crystal which has a XRPD pattern with at least one specific peak at about 2-theta=6.1°, measured using CuKα radiation.

According to the invention there is provided a crystalline form, Form B, of Compound A: 6-hydroxy-2-naphthoic acid (1:1) co-crystal which has a XRPD pattern with at least two specific peaks at about 2-theta=15.2 and 6.1° measured using CuKα radiation.

According to the invention there is provided a crystalline form, Form B, of Compound A: 6-hydroxy-2-naphthoic acid (1:1) co-crystal which has a XRPD pattern with specific peaks at about 2-theta=15.2, 6.1, 16.8, 12.2, 26.1, 28.4, 18.3, 3.1 and 20.7°, measured using CuKα radiation.

According to the invention there is provided a crystalline form, Form B of Compound A: 6-hydroxy-2-naphthoic acid (1:1) co-crystal which has an XRPD pattern substantially the same as the X-ray powder diffraction pattern shown in FIG. 11, measured using CuKα radiation.

According to the invention there is provided a crystalline form, Form B, of Compound A: 6-hydroxy-2-naphthoic acid (1:1) co-crystal which has a XRPD pattern with at least one specific peak at 2-theta=15.2° plus or minus 0.2° 2-theta, measured using CuKα radiation.

According to the invention there is provided a crystalline form, Form B, of Compound A: 6-hydroxy-2-naphthoic acid (1:1) co-crystal which has a XRPD pattern with at least one specific peak at 2-theta=6.1° plus or minus 0.2° 2-theta, measured using CuKα radiation.

According to the invention there is provided a crystalline form, Form B, of Compound A: 6-hydroxy-2-naphthoic acid (1:1) co-crystal which has a XRPD pattern with at least two specific peaks at 2-theta=15.2° and 6.1° plus or minus 0.2° 2-theta, measured using CuKα radiation.

According to the invention there is provided a crystalline form, Form B, of Compound A: 6-hydroxy-2-naphthoic acid (1:1) co-crystal which has a XRPD pattern with specific peaks at 2-theta=15.2, 6.1, 16.8, 12.2, 26.1, 28.4, 18.3, 3.1 and 20.7° wherein said values may be plus or minus 0.2° 2-theta, measured using CuKα radiation.

In a further aspect of the invention the co-crystal of Compound A with 6-hydroxy-2-naphthoic acid is in a crystalline form, Form C.

According to the invention there is provided a crystalline form, Form C, of Compound A:6-hydroxy-2-naphthoic acid (1:1) co-crystal.

According to the invention there is provided a crystalline form, Form C, of Compound A: 6-hydroxy-2-naphthoic acid (1:1) co-crystal which has a XRPD pattern with at least one specific peak at about 2-theta=8.2° measured using CuKα radiation.

According to the invention there is provided a crystalline form, Form B, of Compound A: 6-hydroxy-2-naphthoic acid (1:1) co-crystal which has a XRPD pattern with at least one specific peak at about 2-theta=24.8°, measured using CuKα radiation.

According to the invention there is provided a crystalline form, Form C, of Compound A: 6-hydroxy-2-naphthoic acid (1:1) co-crystal which has a XRPD pattern with at least two specific peaks at about 2-theta=8.2 and 24.8° measured using CuKα radiation.

According to the invention there is provided a crystalline form, Form B, of Compound A: 6-hydroxy-2-naphthoic acid (1:1) co-crystal which has a XRPD pattern with specific peaks at about 2-theta=8.2, 24.8, 18.9, 29.0, 14.8, 15.5 and 16.3°, measured using CuKα radiation.

According to the invention there is provided a crystalline form, Form C of Compound A: 6-hydroxy-2-naphthoic acid (1:1) co-crystal which has an XRPD pattern substantially the same as the X-ray powder diffraction pattern shown in FIG. 13.

According to the invention there is provided a crystalline form, Form C, of Compound A: 6-hydroxy-2-naphthoic acid (1:1) co-crystal which has a XRPD pattern with at least one specific peak at 2-theta=8.2° plus or minus 0.2° 2-theta, measured using CuKα radiation.

According to the invention there is provided a crystalline form, Form C, of Compound A: 6-hydroxy-2-naphthoic acid (1:1) co-crystal which has a XRPD pattern with at least one specific peak at 2-theta=24.8° plus or minus 0.2° 2-theta, measured using CuKα radiation.

According to the invention there is provided a crystalline form, Form C, of Compound A: 6-hydroxy-2-naphthoic acid (1:1) co-crystal which has a XRPD pattern with at least two specific peaks at 2-theta=8.2 and 24.8° plus or minus 0.2° 2-theta, measured using CuKα radiation.

According to the invention there is provided a crystalline form, Form C, of Compound A: 6-hydroxy-2-naphthoic acid (1:1) co-crystal which has a XRPD pattern with specific peaks at 2-theta=8.2, 24.8, 18.9, 29.0, 14.8, 15.5 and 16.3° wherein said values may be plus or minus 0.2° 2-theta, measured using CuKα radiation.

When it is stated that the invention relates to a crystalline form of Compound A:6-hydroxy-2-naphthoic acid (1:1) co-crystal the degree of crystallinity is conveniently greater than about 60%, more conveniently greater than about 80%, preferably greater than about 90% and more preferably greater than about 95%. Most preferably the degree of crystallinity is greater than about 98%.

It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that Compound A, Form A, of the invention is not limited to the crystals that provide X-ray powder diffraction patterns identical to the X-ray powder diffraction pattern shown in FIG. 1, and any crystals providing X-ray powder diffraction patterns substantially the same as those shown in FIG. 1 fall within the scope of the invention. Similarly, it will be understood that the Compound A: 6-hydroxy-2-naphthoic acid (1:1) co-crystal Form A, of the invention is not limited to the crystals that provide X-ray powder diffraction patterns identical to the X-ray powder diffraction pattern shown in FIG. 3 or 9, and any crystals providing X-ray powder diffraction patterns substantially the same as those shown in FIG. 3 or 9 fall within the scope of the invention. Similarly, it will be understood that Compound A: 6-hydroxy-2-naphthoic acid (1:1) co-crystal Forms B and C, of the invention are not limited to the crystals that provide X-ray powder diffraction patterns identical to the X-ray powder diffraction pattern shown in FIGS. 11 and 13 respectively, and any crystals providing X-ray powder diffraction patterns substantially the same as those shown in FIGS. 11 and 13 fall within the scope of the invention. A person skilled in the art of X-ray powder diffraction is able to judge the substantial identity of X-ray powder diffraction patterns.

Persons skilled in the art of X-ray powder diffraction will understand that the relative intensity of peaks can be affected by, for example, grains above 30 microns in size and non-unitary aspect ratios, which may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction pattern in FIGS. 1, 3, 9,11 and 13 and when reading Tables A to E (see Example 1). Furthermore, it should be understood that intensities might fluctuate depending on experimental conditions and sample preparation (preferred orientation).

The compounds of Formula (I) include one or more chiral centres. To the extent a structure or chemical name in this specification does not indicate chirality, the structure or name is intended to encompass any single stereoisomer (i.e. any single chiral isomer) corresponding to that structure or name, as well as any mixture of stereoisomers (e.g. a racemate). It is well-known in the art how such optically-active forms can be prepared. For example, a single stereoisomer can be obtained by isolating it from a mixtures of isomers (e.g. a racemate) using, for example, chiral chromatographic separation. In other embodiments, a single stereoisomer is obtained through direct synthesis from, for example, a chiral starting material.

A particular enantiomer or diastereoismer of a compound described herein may be more active than other enantiomers or diastereoisomers of the same compound.

According to a further aspect of the invention, there is provided a compound of Formula (I), or a pharmaceutically acceptable salt thereof, which is a single enantiomer being in enantiomer excess (% ee) of ≥95%, ≥98%, or ≥99%. Conveniently a single enantiomer is present in an enantiomer excess of ≥99%.

According to a further aspect of the invention, there is provided a compound of Formula (I), or a pharmaceutically acceptable salt thereof, which is a single enantiomer being in enantiomer excess (% ee) in the range 95 to 100%.

According to a further aspect of the invention, there is provided a pharmaceutical composition, which comprises a compound of Formula (I) which is a single enantiomer being in enantiomer excess (% ee) of ≥95%, ≥98%, or ≥99% or a pharmaceutically acceptable salt thereof, in association with a pharmaceutically-acceptable diluent or carrier. Conveniently, the single enantiomer is present in an enantiomer excess of ≥99%.

According to a further aspect of the invention, there is provided a pharmaceutical composition, which comprises a compound of Formula (I) which is a single enantiomer being in enantiomer excess (% ee) in the range 95 to 100%, or a pharmaceutically acceptable salt thereof, in association with a pharmaceutically-acceptable diluent or carrier.

The invention is intended to include all isotopes of atoms occurring in the present compounds. Isotopes will be understood to include those atoms having the same atomic number but different mass number. For example, isotopes of hydrogen include tritium and deuterium and isotopes of carbon include $^{13}C$ and $^{14}C$.

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich: Wiley-VCH/VHCA, 2002. A suitable pharmaceutically acceptable salt of a compound of Formula (I) is, for example, an acid-addition salt. An acid addition salt of a compound of Formula (I) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

It will be understood that the compounds of Formula (I), and pharmaceutically acceptable salts thereof, may exist in solvated and unsolvated forms. For example, a solvated form may be a hydrated form. It is to be understood that the invention encompasses all such solvated and unsolvated forms.

The compounds of Formula (I) may be administered in the form of a prodrug, which is a compound which that is broken down in the human or animal body to release the compound of the invention. Such, pharmaceutically acceptable, prodrugs of compounds for Formula (I) also form an aspect of the invention. Various forms of prodrugs are known in the art. For example, see
a) Design of Pro-drugs, edited by H. Bundgaard, (Elsevier, 1985);
b) A Textbook of Drug Design and Development, edited by Krogsgaard-Larsen and H. Bundgaard, Chapter 5 "Design and Application of Pro-drugs", by H. Bundgaard p. 113-191 (1991);
c) H. Bundgaard, *Advanced Drug Delivery Reviews*, 8, 1-38 (1992);
d) H. Bundgaard, et al., *Journal of Pharmaceutical Sciences*, 77, 285 (1988); and
e) N. Kakeya, et al., *Chem. Pharm. Bull.*, 32, 692 (1984).

Another aspect of the invention provides a process for preparing a compound of Formula (I), or a pharmaceutically acceptable salt thereof. A suitable process is illustrated by the following representative process in which, unless otherwise stated, R¹, R² and n have the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated and are within the ordinary skill of an organic chemist.

Compounds of Formula (I) are conveniently made by a coupling reaction, for example, reaction of a compound of Formula (II) with a compound of Formula (IIIa) or Formula (IIIb) in the presence of a trialkyl phosphine, such as trialkyl tributylphosphine, and a diazene reagent, such as (E)-diazene-1,2-diylbis(piperidin-1-ylmethanone, in a suitable solvent, such as dichloromethane, and a suitable temperature, such as 5° C.

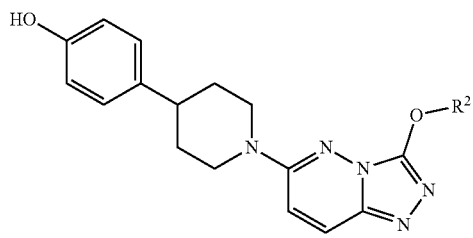

(II)

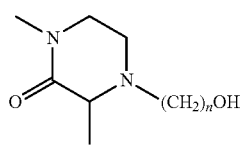

(IIIa)

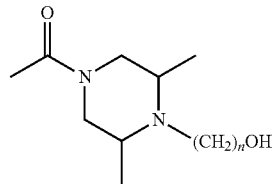

(IIIb)

Compounds of Formula (II) may be made by, for example, reaction of a compound of Formula (IV) with 4-(piperidin-4-yl)phenol in the presence of a base, such as N,N-diisopropylethylamine, in a suitable solvent, such as ethanol, and a suitable temperature, such as 55° C.

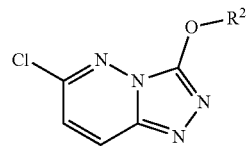

(IV)

Compounds of Formula (IV) may be made by, for example, reaction of 3-chloro-6-hydrazinylpyridazine with a tetramethoxyalkane, such as tetramethoxymethane, at a suitable temperature such as 90° C.

Compounds of Formula (IIIa) can be made by reacting 1,3-dimethylpiperazin-2-one hydrochloride with 2-bromoethanol with a base, such as potassium carbonate, in a solvent, such as 2-methyltetrahydrofuran, at a suitable temperature, such as 100° C.

Compounds of Formula (IIIb) can be made by reacting 1-(3,5-dimethylpiperazin-1-yl)ethanone (compound V) with 2-bromopropan-1-ol with a base, such as potassium carbonate, in a solvent, such as 2-methyltetrahydrofuran, at a suitable temperature, such as 80° C.

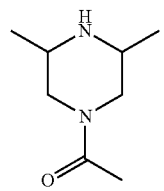

(V)

1-(3,5-dimethylpiperazin-1-yl)ethanone can be made by reacting N-acetyl-N-(2-(trifluoromethyl)phenyl)acetamide with 2,6-dimethylpiperazine in a solvent, such as ethanol, at a suitable temperature, such as ambient temperature.

N-acetyl-N-(2-(trifluoromethyl)phenyl)acetamide can be made by reacting acetyl chloride with 2-(trifluoromethyl) aniline and pyridine in a suitable solvent such as toluene at a suitable temperature, such as 50° C.

4-(Piperidin-4-yl)phenol can be made, for example, according to the following reaction scheme (Scheme 1)

Scheme 1

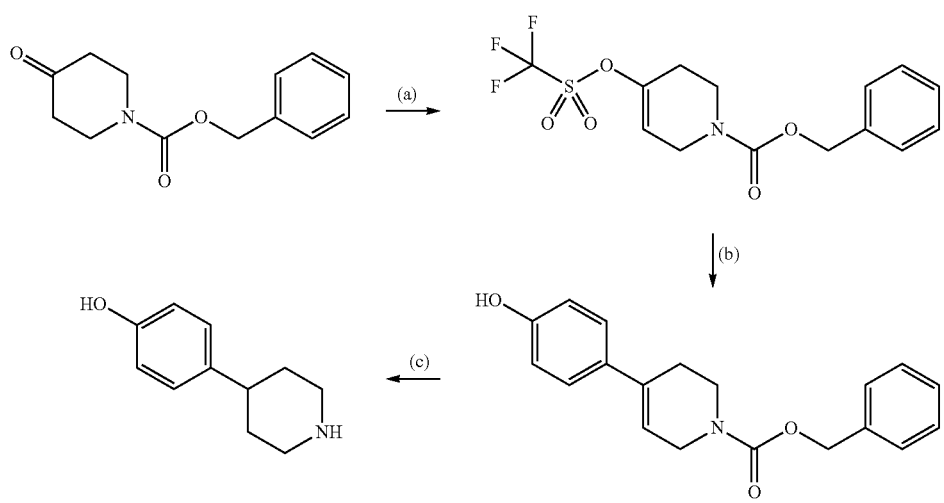

In Scheme (1), the following reaction conditions can be used:— step (a): a base, such as lithium bis(trimethylsilyl)amide and a sulfonylating agent, such as 1,1,1-trifluoro-N-phenyl-N-(trifluoromethylsulfonyl)methanesulfonamide, in the presence of a solvent, such as THF, at a suitable temperature, such as between −78 to 0° C.;

step (b): 4-hydroxyphenylboronic acid in the presence of a palladium II catalyst, such as 1,1'-bis(diphenylphosphino)ferrocenedichloropalladium(II), a base, such as sodium carbonate and a solvent, such as dioxane-water, at a suitable temperature, such as 80° C.; and step (c) hydrogen in the presence of a hydrogenation catalyst, such as 5% palladium on carbon, in a solvent, such as methanol.

Compounds of Formula (I) may also be made by, for example, by reaction of a compound of Formula (VIa) or a compound of Formula (VIb) with a compound of Formula (IV), as described above, in the presence of a base, such as triethylamine, in a suitable solvent, such as dimethyl formamide, and at a suitable temperature, such as 56° C.

(VIa)

(VIb)

Compounds of Formula (VIa) can be made by reacting compounds of -Formula (VIIa) with an acid, such as hydrogen chloride, in the presence of a suitable solvent, such as dioxane, and a suitable temperature such 20° C.

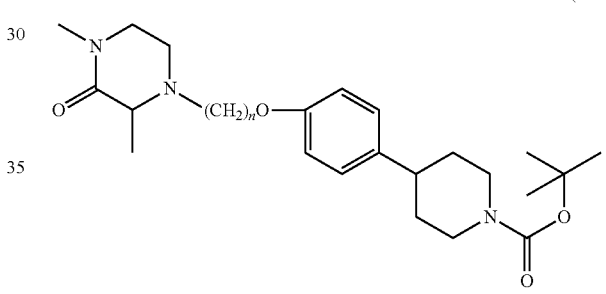

(VIIa)

Compounds of Formula (VIIa) can be made by reacting compounds of Formula (VIIIa) with 1,3-dimethylpiperazine-2-one in the presence of a base, such as N,N-diisopropylethylamine, in the presence of a catalyst, such as potassium iodide, and a solvent, such as dimethylacetamide, and a suitable temperature, such as 120° C.

(VIIIa)

Compounds of Formula (VIIa) can be made by reacting tert-butyl 4-(4-hydroxphenyl)piperidine-1-carboxylate with 1-bromo-3-chloroalkane and a base, such as potassium carbonate, and a solvent, such as dichloromethane, and at a suitable temperature, such as 80° C.

Tert-butyl 4-(4-hydroxphenyl)piperidine-1-carboxylate can be made by reacting 4-(piperidin-4-yl)phenol (made as hereinbefore described) with di-tert-butyl dicarbonate in a suitable solvent, such as dichloromethane, and a suitable temperature, such as 0° C.

Compounds of Formula (VIb) can be made by reacting compounds of Formula (VIIb) in the presence of a suitable solvent, such as methanol, and a suitable catalyst, such as 10% palladium on carbon, under an atmosphere of hydrogen.

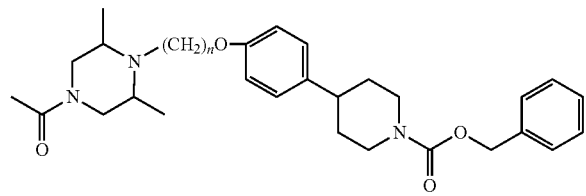

Compounds of Formula (VIIb) can be made by reacting compounds of Formula (VIIIb) with 1-(3,5-dimethylpiperazin-1-yl)ethanone, made as described above, in the presence of a suitable base, such as N,N-diisopropylethylamine, in the presence of a catalyst, such as potassium iodide, and a solvent, such as dimethylacetamide, and at a suitable temperature, such as 120° C.

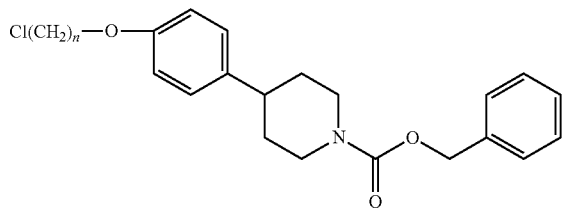

Compounds of Formula (VIIIb) can be made by reacting benzyl 4-(4-hydroxphenyl)piperidine-1-carboxylate with a 1-bromo-3-chloroalkane and a base, such as potassium carbonate, and a solvent, such as dichloromethane, and at a suitable temperature, such as 80° C.

Benzyl 4-(4-hydroxphenyl)piperidine-1-carboxylate can be made by reacting 4-(piperidin-4-yl)phenol (made as hereinbefore described) with benzylchloroformate and DIPEA in a suitable solvent, such as dichloromethane, and a suitable temperature.

As stated above, one aspect of invention is a co-crystal of Compound A with 6-hydroxy-2-naphthoic acid.

The co-crystal can be prepared by mixing Compound A in a suitable solvent with 6-hydroxy-2-naphthoic acid in a suitable solvent. Thus, according to a further aspect of the invention, there is provided a method of preparing a co-crystal of Compound A with 6-hydroxy-2-naphthoic acid, the method comprising the step of mixing a solution of Compound A which is in suitable solvent with 6-hydroxy-2-naphthoic acid which is in a suitable solvent. Suitable solvents would include solvents that solubilise both components and do not form solvates with either Compound A or 6-hydroxy-2-naphthoic acid. According to a further aspect of the invention there is provided a Compound A: 6-hydroxy-2-naphthoic acid co-crystal obtainable by the steps of i) mixing a solution of Compound A in suitable solvent with 6-hydroxy-2-naphthoic acid in a suitable solvent; and ii) drying the resultant mixture from step (i) to obtain a solid.

In one aspect of the invention the suitable solvent is methanol.

Compound A:6-hydroxy-2-naphthoic acid (1:1) co-crystal was found to have a number of advantageous properties compared to the free base form of Compound A. In particular, it was found to be significantly less hydroscopic than Compound A free base. The co-crystal was also found to be more stable than Compound A free base when exposed to range of temperature and humidity conditions.

Biological Assays—

The following assays were used to measure the effects of the compounds of the present invention.

BROMOscan™ Assay (Ex Discoverx)

The ability of the compounds to bind to a bromodomain protein was tested by Discoverx using their proprietory ligand binding site-directed competition assay. Supplied compounds were anonymised.

The BROMOscan assay is based on the principle that test compounds that bind the bromodomain protein prevent its binding to an immobilized ligand thus reducing the amount of protein captured on a solid support. Conversely, test molecules that do not bind the bromodomain have no effect on the amount of protein captured on the solid support. Screening "hits" are identified by measuring the amount of bromodomain captured in test versus control samples by using a quantitative, precise and ultra-sensitive qPCR method that detects the associated DNA label. In a similar manner, dissociation constants (Kds) for test compound-bromodomain interactions are calculated by measuring the amount of bromodomain protein captured on the solid support as a function of the test compound concentration.

Alpha-Screen Assay

The ability of the compounds to bind to a bromodomain protein was tested in an AlphaScreen® assay. The assay is based on the interaction between Histidine-tagged bromodomain protein which can bind to Nickel-chelate donor beads, and a Biotinylated acetyl lysine peptide corresponding to a histone amino acid sequence, which can bind to treptavidin-conjugated acceptor beads. The protein-peptide interaction can be detected by light emission at 520-620 nm. In the presence of compounds which bind to BRD4 a lower signal is observed as the protein-peptide interaction is reduced.

1. The assay was performed as follows:—Greiner BioOne (cat no. 784075) compound plates were used. Compounds were prepared using the Labcyte Echo Acoustic Dispenser with compounds in a final volume of 40 nl per well normalised to 0.5% (v/v) DMSO under final assay conditions. Compounds were tested in 12 point singlicate concentration response format.
2. 4 µl of BRD4 protein (6His-TEV-BRD4, amino acid residues 42-169, corresponding to the BD1 domain) (final assay concentration=50 nM) per well was added using the Beckman Coulter BioRAPTR® Flying Reagent Dispenser Microfluidic Workstation.
3. Incubated for 30 minutes at room temperature.
4. Added 4 µl of acetyl lysine peptide (H4K5,8,12,16(Ac)$_4$-biotin:(NH2-) YSGRG(K-Ac)GG(K-Ac)GLG(K-Ac) GGA(K-Ac)RHR(K-Biotin) (—COOH)) (final assay concentration=50 nM) per well using the Beckman Coulter BioRAPTR® Flying Reagent Dispenser Microfluidic Workstation.
5. Incubated for 30 minutes at room temperature.

6. Added 4 μl of Nickel & Streptavidin-bead solution pre-mixed (beads supplied by Perkin Elmer) per well using the BioRaptr as before (final assay concentration=4 μg/ml). Kept plates in the dark after addition.
7. Incubated for 60 minutes at room temperature keeping the assay plate in the dark
8. Plates were then read using the Perkin Elmer Envision plate reader, laser excitation at 680 nm and emission detected at 520-620 nm.
9. Data was analysed using Genedata software and $IC_{50}$ values calculated.

Anti-Proliferative Assay

The anti-proliferative effect of the compounds was assessed by AlamarBlue assay in MM1.S cells which were originally derived from a multiple myeloma patient. This assay is based on Resazurin, a non-fluorescent indicator dye converted to bright red-fluorescent resorufin via the reduction reactions of metabolically active cells. The amount of fluorescence produced is proportional to the number of living cells. MM.1S cells are cultured in RPMI-1640 medium (Gibco®) plus 10% Fetal bovine serum (FBS) and 1 mM L-glutamine. 12-24 hours before compound dosing, 90 μL of cell suspension (18,750 cells) was seeded into 96-well microtiter plates (black, flat bottom). On the day of compound dosing, compounds were serially diluted 1:3 in 100% DMSO using columns 2-10 of a 96-well microtiter plate. Column 11 of compound serial plate contained only DMSO. All wells were then further diluted 1:30 in media. 10 μL of compound or DMSO alone in media was added to cell plates columns 2-11 in triplicate. In addition, 1 plate had 10 μL of media added and was developed using alamar blue. Plates developed on the day of compound addition were referred to as Day 0. Dosed plates were cultured 3 days under normal conditions (RPMI-1640 plus 10% FBS and 1 mM L-glutamine) After 3 days of culture, dosed plates are developed using either MTS or alamar blue. For each compound concentration, % net growth was calculated by (Day 3 dosed well-Average Day 0)/(Average Day 3 DMSO control-Average Day 0). The $GI_{50}$, the concentration that causes 50% of growth inhibition, of each compound was calculated using the % net growth as defined by National Cancer Institute (NCI).

Assay Monitoring cMyc Protein Modulation

Multiple myeloma MM1.S cells were cultured in RPMI-1640 medium containing 10% FBS and 1% L-glutamine under standardized conditions in a humidified incubator (37° C. and 5% $CO_2$). The impact of cMyc protein modulation induced by bromodomain inhibitors was assessed by staining and quantifying c-Myc protein level after compound treatment using a flow cytometer Assay, carried out in 96-well plate format with 200K cells per well. Cells were treated with serially diluted compounds 16 hours before fixing with 2% paraformaldehyde (final concentration) for 10 minutes at 37° C. After being permeablized by ice cold 90% methanol at 4° C. for 30 min, cells were washed, blocked by buffer (0.5% FBS in phosphate-buffered saline (PBS) buffer) for 10 minutes at room temperature, and stained with cMyc antibody for 1 hour (Cell Signaling Technology®5605, 1:200 dilution). Cells were washed and stained by incubating with Alexa-488 conjugated anti-Rabbit IgG (Cell Signaling Technology®#4412, 1:1000 dilution) at RT for 30 minutes. After staining, cells were washed again and fixed with 2% paraformaldehyde in PBS and ready for analysis by BD FACSCalibur™ flow cytometer. Fluorescence geometric mean was calculated through FlowJo (TreeStar Inc), maximal inhibition signal was determined by control compound treatment at high dose across each plate, and minimal inhibition signal was determined by DMSO treatment. IC50 was calculated by fitting the dose-response data points which are normalized against max and min signals as percentage of inhibition using a standard 4-Parameter-Logistic nonlinear regression model.

Although the pharmacological properties of the compounds of the Formula (I) vary with structural change as expected, in general, activity possessed by compounds of the Formula (I) may be demonstrated at the following concentrations or doses in one or more of the above tests.

The following data was generated for the Examples (the data below may be a result from a single experiment or an average of multiple repeat experiments):

TABLE X

| Example | Alpha screen BRD4 (1) $IC_{50}$/μM | DiscoverX $K_D$/μM | | | | | | | |
|---|---|---|---|---|---|---|---|---|---|
| | | BRD4 (1) | BRD4 (2) | BRD2 (1) | BRD2 (2) | BRD3 (1) | BRD3 (2) | BRDT (1) | BRDT (2) |
| 1 | 0.12 (n = 2) | 0.047 (n = 2) | 0.13 (n = 4) | 0.10 (n = 2) | 0.28 (n = 2) | 0.064 (n = 2) | 0.43 (n = 2) | 0.095 (n = 2) | 0.45 (n = 2) |
| 2 | 0.035 (n = 2) | 0.026 (n = 6) | 0.29 (n = 6) | 0.083 (n = 2) | 0.35 (n = 2) | 0.057 (n = 2) | 0.92 (n = 2) | 0.035 (n = 2) | 1.1 (n = 2) |
| 3 | 0.30 (n = 2) | 0.11 (n = 2) | 0.34 (n = 4) | 0.16 (n = 2) | 0.53 (n = 2) | 0.11 (n = 2) | 0.67 (n = 2) | 0.093 (n = 2) | 0.99 (n = 2) |
| 4 | 0.14 (n = 4) | 0.057 (n = 2) | 0.25 (n = 2) | | | | | | |

Number of repeats in parentheses

TABLE Y

| Example | MM1.S Antiproliferative $GI_{50}$/μM | MM1.S "MoA" $IC_{50}$/μM |
|---|---|---|
| 1 | 0.0049 (n = 9) | 0.011 (n = 12) |
| 2 | <0.0020 (n = 3) | <0.0020 (n = 4) |
| 3 | 0.0075 (n = 2) | 0.025 (n = 1) |
| 4 | 0.0051 (n = 3) | 0.012 (n = 2) |

Number of repeats in parentheses

Xenograft Models

Compound A was also investigated in a xenograft model as described below.

Female CB17 SCID mice aged 6 to 8 weeks were obtained from Charles River Laboratories (Wilmington, Mass.) and maintained under specific-pathogen-free conditions in an AAALAC (Association for Assessment and Accreditation of Laboratory Animal Care)—accredited facility. Irradiated food and autoclaved water were provided ad libitum.

Figure 5:
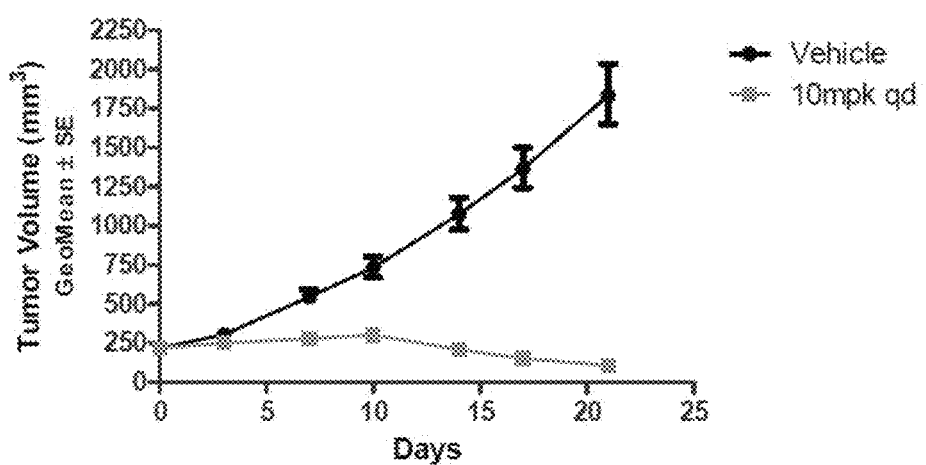
FIG. 5: Tumour Growth Inhibition in a mouse xenograft model by compound A.

MV-4-11 cells (American Tissue Culture Consortium) were resuspended in 0.1 ml of medium without serum and Matrigel (Becton Dickinson) at a 1:1 ratio. Cells ($10^7$/mouse) were injected subcutaneouly into the right flank of mice. Tumors were allowed to grow until they reached an average volume of 200 mm$^3$ for efficacy and then the mice were randomized into groups of 8. Compound A was solubilized in 0.5% HPMC/0.1% Tween80 for dosing. For efficacy, either vehicle or Compound A was administered PO once a day (qd) for 21 days at 10 mg/kg (mpk). Body weight and tumour volume were measured twice a week for 21 days. The results are shown in FIG. 5 and demonstrate the effect of Compound A on tumour volume.

According to a further aspect of the invention there is provided a pharmaceutical composition, which comprises a compound of Formula (I), or a pharmaceutically acceptable salt thereof, as defined herein, in association with a pharmaceutically acceptable diluent or carrier. According to a further aspect of the invention, there is provided a pharmaceutical composition, which comprises a Compound A:6-hydroxy-2-naphthoic acid co-crystal, as defined herein, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In one aspect of the invention the pharmaceutical composition of the invention is a composition suitable for oral use.

The compositions of the invention may be obtained by conventional procedures using conventional pharmaceutical excipients, well known in the art. Thus, compositions intended for oral use may contain, for example, one or more colouring, sweetening, flavouring and/or preservative agents.

For further information on formulation the reader is referred to Chapter 25.2 in Volume 5 of Comprehensive Medicinal Chemistry (Corwin Hansch; Chairman of editorial Board), Pergamon Press 1990.

The compound of Formula (I) or the Compound A:6-hydroxy-2-naphthoic acid co-crystal will normally be administered to a warm-blooded animal at a unit dose within the range of 5 to 5000 mg/m$^2$ body area of the animal i.e. approximately 0.1 to 100 mg/kg, and this normally provides a therapeutically effective dose. A unit dose form, such as a tablet or a capsule, will usually contain 0.5 mg to 250 mg and, such as, 1 to 250 mg of active ingredient. The daily dose will necessarily be varied depending upon the animal or patient host treated, the particular route of administration, and the severity of the illness being treated. Accordingly, the practitioner who is treating any particular animal or patient may determine the optimum dosage. The compounds or co-crystals of the present invention are potentially of value as anti-proliferative agents and/or cell killing agents in the containment and/or treatment of haematological cancers (also referred to as liquid cancers) and solid tumour disease.

Particularly, the compounds or co-crystals of the invention are expected to be useful in the prevention or treatment of those tumours which are associated with amplification of one or more of the BET family of bromodomain containing proteins, suitably BRD4 amplification, or are dependent on key oncogenes which can be regulated by one or more of the BET family of bromodomain containing proteins, suitably BRD4, for example, ovarian, acute myeloid and mixed lineage leukemia (AML), multiple myeloma (MM), diffuse large B-cell lymphoma (DLBCL), castration-resistant prostate cancer (CRPC), non-small cell lung cancer (NSCLC), small cell lung cancer (SCLC), breast cancer, glioblastoma, and neuroblastoma.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

The term 'effective amount' refers to the amount of a compound of Formula (I) or co-crystal as described in any of the embodiments herein which is effective to potentially provide therapy in a subject. In the case of cancer, the effective amount may cause any of the changes observable or measurable in a subject as described in the definition of "therapy", "treatment" and "prophylaxis" For example, the effective amount can potentially reduce the number of cancer or tumour cells; potentially reduce the overall tumour size; potentially inhibit or stop tumour cell infiltration into peripheral organs including, for example, the soft tissue and bone; potentially inhibit and stop tumour metastasis; potentially inhibit and stop tumour growth; potentially relieve to some extent one or more of the symptoms associated with the cancer; potentially reduce morbidity and mortality; potentially improve quality of life; or a combination of such effects. An effective amount may be an amount sufficient to decrease the symptoms of a disease responsive to inhibition of one or more bromodomain-containing proteins. For cancer therapy, efficacy in-vivo can, for example, be measured by assessing the duration of survival, time to disease progression (TTP), the response rates (RR), duration of response, and/or quality of life.

According to the present invention, there is provided a compound of Formula (I), or a pharmaceutically acceptable salt thereof, or a compound of Formula (I): co-former co-crystal, suitably a Compound A:6-hydroxy-2-naphthoic acid co-crystal, as defined hereinbefore, for use in therapy.

According to a further aspect of the invention, there is provided a compound of Formula (I), or a pharmaceutically acceptable salt thereof, or a Compound A:6-hydroxy-2-naphthoic acid co-crystal, as defined hereinbefore, for the manufacture of a medicament.

According to the present invention, there is provided a compound of Formula (I) or a pharmaceutically acceptable salt thereof, or a Compound A:6-hydroxy-2-naphthoic acid co-crystal, as defined hereinbefore, for use as a medicament in a warm-blooded animal such as man.

According to a further aspect of the invention, there is provided a compound of Formula (I), or a pharmaceutically acceptable salt thereof, or a Compound A:6-hydroxy-2-naphthoic acid co-crystal, as defined hereinbefore, for use in the production of anti-proliferative or cell-killing effect in a warm-blooded animal such as man.

According to a further aspect of the invention there is provided the use of a compound of Formula (I), or a pharmaceutically acceptable salt thereof, or a Compound A:6-hydroxy-2-naphthoic acid co-crystal, as defined hereinbefore, in the manufacture of a medicament for use in the production of an anti-proliferative or cell-killing effect in a warm-blooded animal such as man.

According to a further aspect of the invention, there is provided the use of a compound of Formula (I), or a pharmaceutically acceptable salt thereof, or a Compound A:6-hydroxy-2-naphthoic acid co-crystal, as defined hereinbefore, for the production of an anti-proliferative or cell-killing effect in a warm-blooded animal such as man.

According to a further aspect of the invention there is provided a method for producing an anti-proliferative or cell-killing effect in a warm-blooded animal, such as man, in need of such treatment which comprises administering to said animal an effective amount of a compound of Formula (I), or a pharmaceutically acceptable salt thereof, or a Compound A:6-hydroxy-2-naphthoic acid co-crystal, as defined hereinbefore.

According to a further aspect of the invention there is provided a compound of Formula (I), or a pharmaceutically acceptable salt thereof, or a Compound A:6-hydroxy-2-naphthoic acid co-crystal, as defined hereinbefore, for use in the prevention or treatment of cancer in a warm blooded animal such as man.

According to a further aspect of the invention there is provided the use of a compound of Formula (I), or a pharmaceutically acceptable salt thereof, or a Compound A:6-hydroxy-2-naphthoic acid co-crystal, as defined hereinbefore, in the manufacture of a medicament for use in the prevention or treatment of cancer in a warm-blooded animal such as man.

According to a further aspect of the invention there is provided a method for the prevention or treatment of cancer in a warm-blooded animal, such as man, in need of such treatment which comprises administering to said animal an effective amount of a compound of Formula (I), or a pharmaceutically acceptable salt thereof, or a Compound A:6-hydroxy-2-naphthoic acid co-crystal, as defined hereinbefore.

According to a further aspect of the invention there is provided a compound of Formula (I), or a pharmaceutically acceptable salt thereof, or a Compound A:6-hydroxy-2-naphthoic acid co-crystal, as defined hereinbefore, for use in the prevention or treatment of haematological cancers (also referred to a liquid cancers) and solid cancers in a warm blooded animal such as man.

According to a further aspect of the invention there is provided the use of a compound of Formula (I), or a pharmaceutically acceptable salt thereof, or a Compound A:6-hydroxy-2-naphthoic acid co-crystal, as defined hereinbefore, in the manufacture of a medicament for use in the prevention or treatment of haematological and solid cancers in a warm-blooded animal such as man.

According to a further aspect of the invention there is provided a method for the prevention or treatment of haematological and solid cancers in a warm-blooded animal, such as man, in need of such treatment which comprises administering to said animal an effective amount of a compound of Formula (I), or a pharmaceutically acceptable salt thereof, or a Compound A:6-hydroxy-2-naphthoic acid co-crystal, as defined hereinbefore.

One aspect of the invention provides compounds of Formula (I) that potentially inhibit one or more bromodomain-containing proteins, i.e. the BET family of bromodomain-containing proteins, and such as BRD2, BRD3, BRD4, and BRDt and, suitably BRD4. Advantageously such compounds may be useful for the treatment of a proliferative disorder such as cancer in a patient where the proliferative disorder is a bromodomain-containing protein mediated disorder. By 'bromodomain-containing protein mediated disorder' is meant any disease or other deleterious condition in which one or more of the bromodomain-containing proteins are known to play a role.

According to a further aspect of the invention there is provided a compound of Formula (I), or a pharmaceutically acceptable salt thereof, or a Compound A:6-hydroxy-2-naphthoic acid co-crystal, as defined hereinbefore, for use in the prevention or treatment of a BET dependent cancer in a warm blooded animal such as man.

By BET dependent cancer we mean any cancer in which one or more of the BET family of bromodomain-containing proteins such as BRD2, BRD3, BRD4, and BRDt play a role.

According to a further aspect of the invention there is provided a compound of Formula (I), or a pharmaceutically acceptable salt thereof, or a Compound A:6-hydroxy-2-naphthoic acid co-crystal, as defined hereinbefore, for use in the prevention or treatment of a BRD4 dependent cancer in a warm blooded animal such as man.

According to a further aspect of the invention there is provided the use of a compound of Formula (I), or a pharmaceutically acceptable salt thereof, or a Compound A:6-hydroxy-2-naphthoic acid co-crystal, as defined hereinbefore, in the manufacture of a medicament for use in the prevention or treatment of a BET dependent cancer in a warm-blooded animal such as man.

According to a further aspect of the invention there is provided the use of a compound of Formula (I), or a pharmaceutically acceptable salt thereof, or a Compound A:6-hydroxy-2-naphthoic acid co-crystal, as defined hereinbefore, in the manufacture of a medicament for use in the prevention or treatment of a BRD4 dependent cancer in a warm-blooded animal such as man.

According to a further aspect of the invention there is provided a method for the prevention or treatment of BET dependent cancer in a warm-blooded animal, such as man, in need of such treatment which comprises administering to said animal an effective amount of a compound of Formula (I), or a pharmaceutically acceptable salt thereof, or a Compound A:6-hydroxy-2-naphthoic acid co-crystal, as defined hereinbefore.

According to a further aspect of the invention there is provided a method for the prevention or treatment of BRD4 dependent cancer in a warm-blooded animal, such as man, in need of such treatment which comprises administering to said animal an effective amount of a compound of Formula (I), or a pharmaceutically acceptable salt thereof, or a Compound A:6-hydroxy-2-naphthoic acid co-crystal, as defined hereinbefore.

According to a further aspect of the invention there is provided a compound of Formula (I), or a pharmaceutically acceptable salt thereof, or a Compound A:6-hydroxy-2-naphthoic acid co-crystal, as defined hereinbefore, for use in providing an inhibitory effect on one or more of the BET family of bromodomain-containing proteins.

According to a further aspect of the invention there is provided a compound of Formula (I), or a pharmaceutically acceptable salt thereof, or a Compound A:6-hydroxy-2-naphthoic acid co-crystal, as defined hereinbefore, for use in providing an inhibitory effect on BRD4.

According to a further aspect of the invention there is provided the use of a compound of Formula (I), or a pharmaceutically acceptable salt thereof, or a Compound A:6-hydroxy-2-naphthoic acid co-crystal, as defined hereinbefore, in the manufacture of a medicament for use in providing an inhibitory effect on one or more of the BET family of bromodomain-containing proteins.

According to a further aspect of the invention there is provided the use of a compound of Formula (I), or a pharmaceutically acceptable salt thereof, or a Compound A:6-hydroxy-2-naphthoic acid co-crystal, as defined hereinbefore, in the manufacture of a medicament for use in providing an inhibitory effect on BRD4.

According to a further aspect of the invention there is provided a method for providing an inhibitory effect on one or more of the BET family of bromodomain-containing proteins which comprises administering to said animal an effective amount of a compound of Formula (I), or a pharmaceutically acceptable salt thereof, or a Compound A:6-hydroxy-2-naphthoic acid co-crystal, as defined hereinbefore.

According to a further aspect of the invention there is provided a method for providing an inhibitory effect on BRD4 which comprises administering to said animal an effective amount of a compound of Formula (I), or a pharmaceutically acceptable salt thereof, or a Compound A:6-hydroxy-2-naphthoic acid co-crystal, as defined hereinbefore.

The Compound A:6-hydroxy-2-naphthoic acid co-crystal can be in Form A, B or C, as herein defined and suitably is in Form A.

The anti-cancer treatment described herein may be applied as a sole therapy or may involve, in addition to the compounds of the invention, conventional surgery or radiotherapy or chemotherapy or immunotherapy. Such chemotherapy could be administered concurrently, simultaneously, sequentially or separately to treatment with the compound of the invention.

Where a combination therapy is used, the amount of the compound of Formula (I) or pharmaceutically acceptable salt thereof or Compound A:6-hydroxy-2-naphthoic acid co-crystal described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of one or more bromodomain-containing proteins. Typically, such amounts may be determined by one skilled in the art by, for example, starting with the dosage range described in this specification for the compound of Formula (I) or pharmaceutically acceptable salt thereof or a Compound A:6-hydroxy-2-naphthoic acid co-crystal as herein defined and an approved or otherwise published dosage range(s) of the other pharmaceutically active compound(s).

In a further aspect of the invention there is provided a pharmaceutical product comprising the compound of Formula (I), and an additional anti-tumour substance, for the conjoint treatment of cancer.

In such an aspect of the invention there is provided a pharmaceutical product comprising the compound of Formula (I), or a pharmaceutically acceptable salt thereof, as defined hereinbefore, and an additional anti-tumour agent, for the conjoint treatment of cancer.

In such aspects the pharmaceutical product comprises a compound of Formula (I) and co-former in form of a co-crystal.

In a further aspect of the invention there is provided a pharmaceutical product comprising a Compound A:6 hydroxy-2-naphthoic acid co-crystal, as defined hereinbefore, and an additional anti-tumour substance, for the conjoint treatment of cancer.

Such conjoint treatment may involve one or more of the following anti-tumour agent:—

(i) antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil, pemetrexel and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); and topoisomerase inhibitors (for example epipodophyllotoxins like etoposide and teniposide, amsacrine, topotecan and camptothecin and irinotecan); inhibitors of DNA repair mechanisms such as CHK kinase; DNA-dependent protein kinase inhibitors; inhibitors of poly (ADP-ribose) polymerase (PARP inhibitors, including olaparib); and Hsp90 inhibitors such as tanespimycin and retaspimycin;

(ii) compounds that inhibit progression through the cell cycle such as antimitotic agents (for example vinca alkaloids like vincristine, vinblastine, vindesine and vinorelbine; epothilones such as ixabepilone and patupilone; taxoids like taxol, taxotere and docetaxel; polo-like kinase inhibitors; and inhibitors of kinesin motor proteins such as Eg5 protein inhibitors); aurora kinase inhibitors (for example AZD1152, PH739358, VX-680, MLN8054, R763, MP235, MP529, VX-528 AND AX39459); cyclin dependent kinase inhibitors such as CDK2 and/or CDK4 inhibitors; and inhibitors of centromeric protein function such as CENP-E inhibitors;

(iii) cytostatic agents that alter hormone-dependent growth such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane); inhibitors of 5α-reductase such as finasteride and CYP17A1 inhibitors such as abiraterone;

(iv) anti-invasion agents, for example c-Src kinase family inhibitors like AZD0530 (saracatinib); dasatinib ((BMS-354825), J. Med. Chem., 2004, 47, 6658-6661) and bosutinib (SKI-606), and metalloproteinase inhibitors like marimastat, inhibitors of urokinase plasminogen activator receptor function or antibodies to heparanase; inhibitors of FAK or focal-adhesion kinase; small molecule inhibitors of MET receptor kinase (for example volitinib/AZD6904); antibodies to MET receptor kinase or the MET ligand hepatocyte growth factor (for example onartuzumab);

(v) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as gefitinib (ZD1839), erlotinib (OSI-774) and CI 1033, erbB2 tyrosine kinase inhibitors such as lapatinib; mixed erbB 1/2 inhibitors such as afatanib; and irreversible inhibitors of EGFR and Her2 such as HKI-272, irreversible inhibitors of EGFR such as AZD9291; inhibitors of the hepatocyte growth factor family and their receptors; inhibitors of the insulin growth factor family including small molecule kinase inhibitors and antibodies directed to insulin-like growth factors and insulin-like growth factor receptors; inhibitors of the platelet-derived growth factor family and their receptors such as imatinib and/or nilotinib (AMN107); c-kit inhibitors, AnLK inhibitors, Flt3 kinase inhibitors, c-abl kinase inhibitors, and inhibitors of CSF-1R or TRK kinase;

(vi) inhibitors of signal transduction kinases as FGFR (for example AZD4547), PIM (for example AZD1208), MEK (for example Selumetinib (AZD6244), AKT (for example AZD5363), inhibitors of TOR kinases (including TORC1 and TORC2, for example AZD2014), and inhibitors of PI3 kinase, including isoforms such as PI3K-α, PI3K-β or PI3K-δ (for example AZD8186); inhibitors of serine/threonine kinases such as Ras or Raf kinases (for example sorafenib or vemurafenib); Inhibitors of PDK, SGK, PI4K or PIP5K, JAK, STAT (including STAT3, an inhibitor of which is AZD9150) and IRAK4; ATR inhibitors (for example AZD6738) or ATM inhibitors, BTK inhibitors such as ibrutinib, SYK inhibitors such as fostamatinib, and cyclin dependent kinase inhibitors; farnesyl transferase inhibitors such as tipifarnib (R115777) lonafarnib (SCH66336) and Wee-li kinase inhibitors (for example AZD1775 as described in WO2007/126128);

(vii) antiangiogenic agents such as those which inhibit the effects of vascular endothelial growth factor, for example the anti-vascular endothelial cell growth factor antibody bevacizumab (Avastin™) and for example, a VEGF receptor tyrosine kinase inhibitor such as vandetanib (ZD6474), sorafenib, vatalanib (PTK787), sunitinib (SU11248), axitinib (AG-013736), pazopanib (GW 786034) and cediranib (AZD2171), compounds such as those disclosed in WO97/22596, WO97/30035, WO97/32856 and WO98/13354 and compounds that work by other mechanisms (for example linomide, inhibitors of integrin αvβ3 function and angiostatin);

(viii) vascular damaging agents such as Combretastatin A4 and compounds disclosed in WO99/02166, WO00/40529, WO00/41669, WO01/92224, WO02/04434 and WO02/08213;

(ix) antisense therapies, for example those which are directed to the targets listed above, such as ISIS 2503, an anti-ras antisense;

(x) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(xi) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor; approaches to decrease T-cell anergy or regulatory T-cell function; approaches that enhance T-cell responses to tumours, such as blocking antibodies to CTLA4 (for example ipilimumab and tremelimumab), B7H1, PD-1 (for example BMS-936558 or MEDI-4736), and agonist antibodies to CD137; approaches using transfected immune cells such as cytokine-transfected dendritic cells; approaches using cytokine-transfected tumour cell lines, approaches using antibodies to tumour associated antigens, and antibodies that deplete target cell types (e.g., unconjugated anti-CD20 antibodies such as Rituximab, radiolabeled anti-CD20 antibodies Bexxar and Zevalin, and anti-CD54 antibody Campath); R-CHOP chemotherapy regimen (Rituximab together with cyclophosphamide, doxorubicin hydrochloride, vincristine sulphate and prednisone); approaches using anti-idiotypic antibodies; approaches that enhance Natural Killer cell function; and approaches that utilize antibody-toxin conjugates (e.g. anti-CD33 antibody Mylotarg); immunotoxins such as moxetumumab pasudotox; agonists of toll-like receptor 7 or toll-like receptor 9;

(xii) inhibitors of proteasome mediated protein degradation including but not limited to proteasome inhibitors such as Velcade™ (Bortezomib) or carfilzomib, inhibitors of ubiquity lipases, inhibitors of ubiquitin proteases, inhibitors of protein Neddylation, and inhibitors of protein sumoylation; and (xiii) other standard of care agents such as cyclophosphamide, prednisone, lenalidomide or thalidomide.

According to this aspect of the invention there is provided a combination suitable for use in the treatment of cancer comprising a compound of Formula (I) or a pharmaceutically acceptable salt thereof and an additional anti-tumour agent, in particular any one of the anti-tumour agents listed in (i)-(xiii) above.

According to this aspect of the invention there is also a provided a combination suitable for use in the treatment of cancer comprising a Compound A:6-hydroxy-2-naphthoic acid co-crystal and an additional anti-tumour agent, in particular any one of the anti-tumour agents listed in (i)-(xiii) above.

In a further aspect of the invention there is provided a compound of Formula (I) or a pharmaceutically acceptable salt thereof in combination with an additional anti-tumour agent, in particular an anti-tumour agent selected from one listed in (i)-(xiii) above.

In a further aspect of the invention there is provided a compound A: 6-hydroxy-2-naphthoic co-crystal in combination with an additional anti-tumour agent, in particular an anti-tumour agent selected from one listed in (i)-(xiii) above.

According to a further aspect of the invention there is provided a kit comprising a compound of Formula (I), or a pharmaceutically acceptable salt thereof, or a Compound A:6-hydroxy-2-naphthoic co-crystal in combination with an anti-tumor agent. In certain embodiments, the kit additionally comprises instructions for the use of said compound(s) or co-crystal.

According to a further aspect of the invention there is provided a kit comprising:

a) a compound of Formula (I), or a pharmaceutically acceptable salt thereof, or a Compound A:6-hydroxy-2-naphthoic co-crystal in a first unit dosage form;

b) an additional anti-tumor agent in a second unit dosage form; and c) container means for containing said first and second dosage forms.

The invention will now be illustrated in the following examples in which, generally:

(i) temperatures are given in degrees Celsius (° C.); unless stated otherwise, operations were carried out at room or ambient temperature, that is, at a temperature in the range of 18 to 25° C.;

(ii) organic solutions were dried over anhydrous magnesium sulfate or anhydrous sodium sulfate; evaporation of solvent was carried out using a rotary evaporator under reduced pressure (600 to 4000 Pascals; 4.5 to 30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LC-MS, and reaction times where given are for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300, 400 or 500 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; bs, broad singlet; dd, double doublet; td, triple doublet; qd, quartet doublet;

(viii) For the carbon ($^{13}$C) cross polarisation magic angle spinning solid state NMR analysis carried out on Example 1, spectra of the co-crystal, free base of Compound A and co-former were recorded on a Bruker Avance NMR spectrometer operating at a $^1$H frequency of 400 MHz. The samples were spun about the magic angle at a frequency of 9 kHz and a contact pulse of 2 ms was used to allow transfer of magnetisation from proton to carbon. A recycle delay of 5 s was used to allow for spin lattice relaxation;

(ix) For the nitrogen ($^{15}$N) cross polarisation magic angle spinning solid state NMR analysis carried out on Example 1, spectra of the co-crystal were recorded on a Bruker Avance NMR spectrometer operating at a $^1$H frequency of 400 MHz. The samples were spun about the magic angle at a frequency of 5 kHz and a contact pulse of 200 µs and 2 ms was used to allow transfer of magnetisation from proton to carbon. A recycle delay of 5 s was used to allow for spin lattice relaxation;

(x) chemical symbols have their usual meanings; SI units and symbols are used;

(xi) Mass spectra (MS) and LC-MS data were generated on an LC-MS system where the HPLC component comprised generally either an Agilent 1100, Waters Alliance HT (2790 & 2795) equipment or an HP1100 pump and Diode Array with CTC autosampler and was run on a Phenomenex Gemini C18 5 µm, 50×2 mm column (or similar) eluting with either acidic eluent (for example, using a gradient between 0-95% water/acetonitrile with 5% of a 1% formic acid in 50:50 water:acetonitrile (v/v) mixture), or basic eluent (for example, using a gradient between 0-95% water/acetonitrile with 5% of a 0.1% 880 ammonia in acetonitrile mixture); and the MS component comprised generally a Waters ZQ mass spectrometer scanning over an appropriate mass range. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is the (M+H)+ for positive ion mode and (M−H)− for negative ion mode;

(xii) unless stated otherwise compounds containing an asymmetrically substituted carbon have not been resolved;

(xiii) preparative high performance liquid chromatography (HPLC) was performed on a Gilson instrument using the following conditions:—

Column: C18 reversed-phase silica, for example, Waters 'Xbridge', 5 µm silica, 19×100 mm, or 30×100 mm, using decreasingly polar solvent mixtures as eluent (decreasing ratio of solvent A to solvent B); solvent A: water with 1% ammonium hydroxide; solvent B: acetonitrile; flow rate: 28 ml/min or 61 ml/min; gradient: tailored to suit each compound generally 7-10 min in length; wavelength: 254 nm;

(xiv) Strong cation exchange (SCX) chromatography was performed on pre-packed cartridges (for example, ISOLUTE SCX-2 propyl sulfonic acid-based cartridges supplied by International Sorbent Technology), using a basic eluent (for example, 1M ammonia in methanol);

(xv) the following abbreviations have been used herein, where necessary:—

ADDP 1,1'-(azodicarbonyl)dipiperidine
DCM dichloromethane
DIPEA N,N-diisopropylethylamine
DMA N,N-dimethyl acetamide
DMF N,N-dimethylformamide
DME Dimethoxyethane
DMSO dimethylsulphoxide
Et$_2$O diethylether
EtOAc ethyl acetate
EtOH ethanol
HPLC high performance liquid chromatography
MeOH methanol
MgSO$_4$ magnesium sulfate
MTBE methyl tert-butyl ether
NMR nuclear magnetic resonance
SCX strong cation exchange
TFA trifluoroacetic acid
THF tetrahydrofuran;

(xvii) For XRPD analysis of Example 1, the sample was mounted on a silicon wafer mount and analysed using the PANalytical CubiX PRO diffractometer. Samples were measured in reflection geometry in θ-2θ configuration over the scan range 2° to 40° 2θ with a nominal 25 second exposure per 0.02° increment. The sample was spun at 30 revolutions per minute (to improve counting statistics) and irradiated with X-rays generated by a copper long-fine focus tube operated at 45 kV and 40 mA with a wavelength of 1.5418 Å. Persons skilled in the art of X-ray powder diffraction will understand that the relative intensity of peaks can be affected by, for example, grains above 30 microns in size and non-unitary aspect ratios that may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

(xviii) Differential Scanning calorimetry: Analytical Instrument: TA Instruments Q1000 DSC.

Typically less than 5 mg of material contained in a standard aluminium pan fitted with a lid was heated over the temperature range 25° C. to 300° C. at a constant heating rate of 10° C. per minute. A purge gas using nitrogen was used—flow rate 50 ml per minute.

Example 1: Preparation of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one Form A

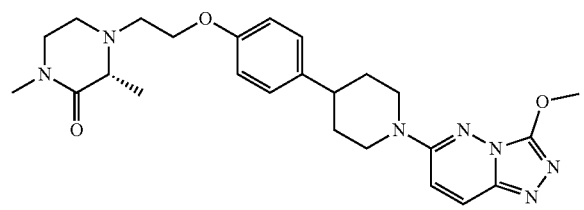

Tributylphosphine (102 mL, 414.92 mmol) was added portionwise to a suspension of 4-(1-(3-methoxy-[1,2,4]triazolo[4,3-b]pyridazin-6-yl)piperidin-4-yl)phenol (67.5 g, 207.46 mmol) in well degassed, anhydrous DCM (1.7 L) at 5° C. under nitrogen. The mixture was cooled to 0° C. and (E)-diazene-1,2-diylbis(piperidin-1-yl methanone) (105 g, 414.92 mmol) was added portionwise. A solution of (R)-4-(2-hydroxyethyl)-1,3-dimethylpiperazin-2-one (46.4 g, 269.70 mmol) in DCM (200 mL) was then added dropwise. The reaction mixture was stirred for 30 minutes and filtered. The clear solution was diluted with further DCM (1 L) and then acidified with 2M HCl (400 mL) and water (400 mL) was added. The combined aqueous solution was washed with DCM (3×1 L) and then EtOAc (1 L). The aqueous solution was then basified with solid Na$_2$CO$_3$ to pH~10 and extracted with DCM (3×1.5 L). The combined organic solution was washed with water (500 mL) and saturated brine (500 mL), then dried over MgSO$_4$ and evaporated to dryness to afford crude material. This was purified by flash silica chromatography, eluting with EtOH:EtOAc:heptane:NH$_{3(aq)}$ 1.8:4:4:0.2. Fractions containing the desired product were evaporated to dryness to give a yellow foam. This was further purified by preparative HPLC (Chiralpak AS column, 20 μm silica, 100 mm diameter, 250 mm length), heptane/EtOH 50/50 at 400 ml/min. Fractions containing the desired product were evaporated to dryness and the resulting solid was stirred as a suspension in diethyl ether (300 mL) for 18 hours, filtered and dried to afford (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one (69 g, 69.4%) as a pale yellow solid. $^1$H NMR (400 MHz, DMSO, 30° C.) 1.22 (3H, d), 1.62 (2H, qd), 1.82 (2H, d), 2.6-2.79 (3H, m), 2.79 (3H, s), 2.85-3.09 (4H, m), 3.13 (1H, q), 3.2-3.26 (2H, m), 4.03 (2H, t), 4.17 (3H, s), 4.28 (2H, d), 6.85 (2H, d), 7.15 (2H, d), 7.29 (1H, d), 7.85 (1H, d). m/z ES+[M+H]+ 480

The 4-(1-(3-methoxy-[1,2,4]triazolo[4,3-b]pyridazin-6-yl)piperidin-4-yl)phenol used as starting material was prepared as follows:—

Preparation of benzyl 4-(trifluoromethylsulfonyloxy)-5,6-dihydropyridine-1(2H)-carboxylate

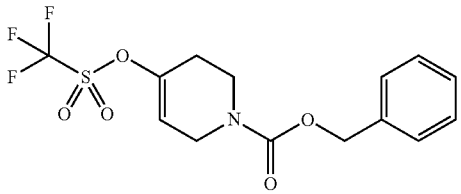 [SMILES: O=C(OCc1ccccc1)N1CC=C(OS(=O)(=O)C(F)(F)F)CC1]

A solution of benzyl 4-oxopiperidine-1-carboxylate (88.57 g, 379.70 mmol) in THF (300 mL) was added dropwise to lithium bis(trimethylsilyl)amide (1M in THF) (418 mL, 417.67 mmol) at −78° C., over a period of 1 hour under nitrogen. The resulting mixture was stirred at −78° C. for 90 minutes then a solution of 1,1,1-trifluoro-N-phenyl-N-(trifluoromethylsulfonyl)methanesulfonamide (142 g, 398.68 mmol) in THF (600 mL) was added dropwise over a period of 1 hour. The resulting mixture was stirred at −78° C. for 30 minutes, then allowed to warm to ambient temperature and stirred for 16 hours. The reaction mixture was quenched with 2M aqueous sodium hydroxide (450 mL). The layers were separated and the organic layer was washed with 2M aqueous sodium hydroxide (360 mL). The solvent was evaporated, then the residue was re-dissolved in Et$_2$O (1500 mL) and the solution washed with water (500 mL). The organic layer was dried over MgSO$_4$, filtered and evaporated to afford benzyl 4-(trifluoromethylsulfonyloxy)-5,6-dihydropyridine-1(2H)-carboxylate (124 g, 81%) as a colourless oil. $^1$H NMR (400 MHz, DMSO, 30° C.) 2.43 (2H, m), 3.62 (2H, m), 4.06 (2H, m), 5.10 (2H, s), 6.02 (1H, m), 7.34 (5H, m).

Preparation of benzyl 4-(4-hydroxyphenyl)-5,6-dihydropyridine-1(2H)-carboxylate

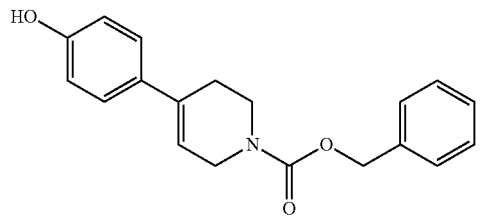 [SMILES: O=C(OCc1ccccc1)N1CC=C(c2ccc(O)cc2)CC1]

Sodium carbonate (96 g, 909.79 mmol) was added to benzyl 4-(trifluoromethylsulfonyloxy)-5,6-dihydropyridine-1(2H)-carboxylate (123.1 g, 303.26 mmol) and 4-hydroxyphenylboronic acid (46.0 g, 333.59 mmol) in a mixture of dioxane (1000 mL) and water (250 mL). The resulting mixture was bubbled with nitrogen for 10 minutes then 1,1'-bis(diphenylphosphino)ferrocenedichloropalladium(II) (5.49 g, 7.58 mmol) was added and the reaction mixture was heated at 80° C. for 1 hour. The reaction mixture was diluted with DCM (2 L) and washed with water (2 L). The aqueous layer was re-extracted with DCM (1 L), then the combined organics were washed with saturated brine (500 mL), dried over MgSO$_4$, filtered and evaporated to afford crude product. The crude product was purified by flash silica chromatography, elution gradient 10 to 30% EtOAc in isohexane. Fractions containing the desired product were evaporated to dryness then triturated with isohexane, filtered and dried to afford benzyl 4-(4-hydroxyphenyl)-5,6-dihydropyridine-1 (2H)-carboxylate (62.3 g, 66.4%) as a white solid. ¹H NMR (400 MHz, DMSO, 30° C.) 2.44 (2H, m), 3.61 (2H, m), 4.05 (2H, m), 5.12 (2H, s), 5.99 (1H, m), 6.73 (2H, d), 7.26 (2H, d), 7.32-7.40 (5H, m), 9.45 (1H, s). m/z: ES+[M+H]+ 310.

Preparation of 4-(piperidin-4-yl)phenol

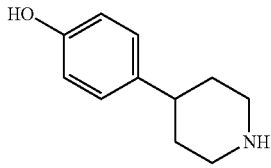 [SMILES: Oc1ccc(C2CCNCC2)cc1]

Benzyl 4-(4-hydroxyphenyl)-5,6-dihydropyridine-1(2H)-carboxylate (37.7 g, 121.86 mmol) and 5% palladium on carbon (7.6 g, 3.57 mmol) in MeOH (380 mL) were stirred under an atmosphere of hydrogen at 5 bar and 25° C. for 2 hours. The catalyst was removed by filtration, washed with MeOH and the solvents evaporated. The crude material was triturated with Et₂O (200 mL), then the desired product collected by filtration and dried under vacuum to afford 4-(piperidin-4-yl)phenol (20.36 g, 94%) as a white solid. ¹H NMR (400 MHz, DMSO, 30° C.) 1.46 (2H, m), 1.65 (2H, m), 2.45 (1H, m), 2.58 (2H, m), 3.02 (2H, m), 6.68 (2H, d), 7.00 (2H, d), 9.15 (1H, s). m/z: ES+[M+H]+ 178

Preparation of 4-(piperidin-4-yl)phenol hydrobromide

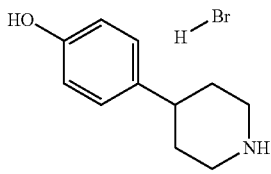

Hydrogen bromide (48% in water) (0.283 mL, 2.48 mmol) was added dropwise to a suspension 4-(piperidin-4-yl)phenol (0.4 g, 2.26 mmol) in THF (23 mL). The resulting suspension was stirred for 30 minutes. The solid was collected by filtration, washed with THF (20 mL) and dried under vacuum to give 4-(piperidin-4-yl)phenol hydrobromide (0.580 g, 100%) as a white powder. 1H NMR (400 MHz, DMSO, 30° C.) 1.74 (2H, qd), 1.86 (2H, d), 2.71 (1H, tt), 2.96 (2H, td), 3.33 (2H, d), 6.68-6.73 (2H, m), 6.97-7.02 (2H, m), 8.48 (2H, br s), 9.18 (1H, br s).

Preparation of 6-chloro-3-methoxy-[1,2,4]triazolo[4,3-b]pyridazine

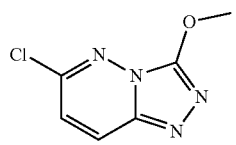

3-Chloro-6-hydrazinylpyridazine (18 g, 124.51 mmol) was suspended in DME (330 mL) and treated with tetramethoxymethane (26.5 mL, 199.22 mmol) and the resulting mixture was stirred at 90° C. for 3 hours. The DME was evaporated off and the residue was dissolved in 5% MeOH/DCM; and then filtered through a silica plug. The filtrate was evaporated to dryness and then taken up in MTBE (200 mL) and slurried for 1 hour. The solid was filtered and dried under vacuum to afford 6-chloro-3-methoxy-[1,2,4]triazolo[4,3-b]pyridazine (19.78 g, 86%) as a cream powder. ¹H NMR (400 MHz, DMSO, 30° C.) 4.25 (3H, s), 7.30 (1H, d), 8.22 (1H, d). m/z: ES+[M+H]+ 185

Preparation of 4-(1-(3-methoxy-[1,2,4]triazolo[4,3-b]pyridazin-6-yl)piperidin-4-yl)phenol

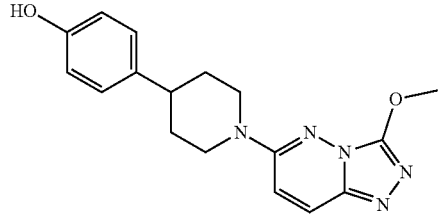 [SMILES: COc1nnc2ccc(N3CCC(c4ccc(O)cc4)CC3)nn12]

6-Chloro-3-methoxy-[1,2,4]triazolo[4,3-b]pyridazine (19.73 g, 106.91 mmol) was added to 4-(piperidin-4-yl)phenol hydrobromide (18.4 g, 71.28 mmol) in EtOH (200 mL). To this mixture was added DIPEA (62.2 mL, 356.38 mmol) and the reaction was stirred at 55° C. for 18 hours. The reaction mixture was then cooled to ambient temperature and poured into vigorously stirred water (1600 mL); and stirred vigourously for 2 hours. The solid precipitate was filtered off and washed sequentially with H₂O (200 mL) and Et₂O (200 mL). The resulting solid was dried under vacuum to afford 4-(1-(3-methoxy-[1,2,4]triazolo[4,3-b]pyridazin-6-yl)piperidin-4-yl)phenol (15.30 g, 66.0%) as a pale brown solid. ¹H NMR (400 MHz, DMSO, 30° C.) 1.59 (2H, qd), 1.81 (2H, d), 2.67 (1H, ddt), 2.9-3.02 (2H, m), 4.17 (3H, s), 4.23-4.31 (2H, m), 6.63-6.71 (2H, m), 7.02 (2H, dd), 7.29 (1H, d), 7.84 (1H, d), 9.14 (1H, s). m/z ES+[M+H]+ 326

The (R)-4-(2-hydroxyethyl)-1,3-dimethylpiperazin-2-one used as starting material was prepared as follows:—

Preparation of (R)-4-(2-hydroxyethyl)-1,3-dimethylpiperazin-2-one

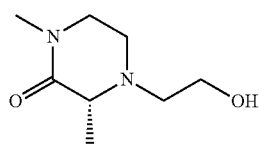

2-Bromoethanol (108 mL, 1518.54 mmol) was added to a mixture of (R)-1,3-dimethylpiperazin-2-one hydrochloride (50 g, 303.71 mmol) and potassium carbonate (126 g, 911.12 mmol) in 2-methyltetrahydrofuran (500 mL). The mixture was stirred at 100° C. for 16 hours. The mixture was filtered and evaporated to dryness to give crude product. This was purified by flash chromatography on silica gel eluting with 1 to 5% MeOH in DCM and pure fractions were combined and evaporated to dryness to afford (R)-4-(2-hydroxyethyl)-1,3-dimethylpiperazin-2-one (36.0 g, 68.8%) as a thick yellow oil. ¹H NMR (400 MHz, DMSO, 30° C.) 1.19 (3H, d), 2.42 (1H, dt), 2.59 (2H, tt), 2.79 (3H, s), 2.93-3.1 (2H, m), 3.17-3.25 (2H, m), 3.47 (2H, q), 4.41 (1H, t).

The final product, (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one, was analysed by XRPD and DSC and found to be crystalline. XRPD of a sample of the material gave rise to a diffraction pattern as shown in FIG. 1. (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one Form A is characterised by at least one peak at a 2θ value of 20.9° or 16.7°, measured using CuKα radiation. The ten most prominent peaks of the XRPD are shown in Table A.

TABLE A

Ten most Prominent XRPD peaks for (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one Form A

| Angle 2-Theta (2θ) | Intensity % |
|---|---|
| 20.9 | 100.0 |
| 16.7 | 53.4 |
| 20.2 | 38.1 |
| 21.2 | 27.2 |
| 27.4 | 26.5 |
| 18.0 | 23.4 |
| 16.8 | 20.0 |
| 23.6 | 18.1 |
| 15.1 | 14.2 |
| 15.5 | 13.9 | wherein the 2-theta values are +/−0.2°.

Figure 2:
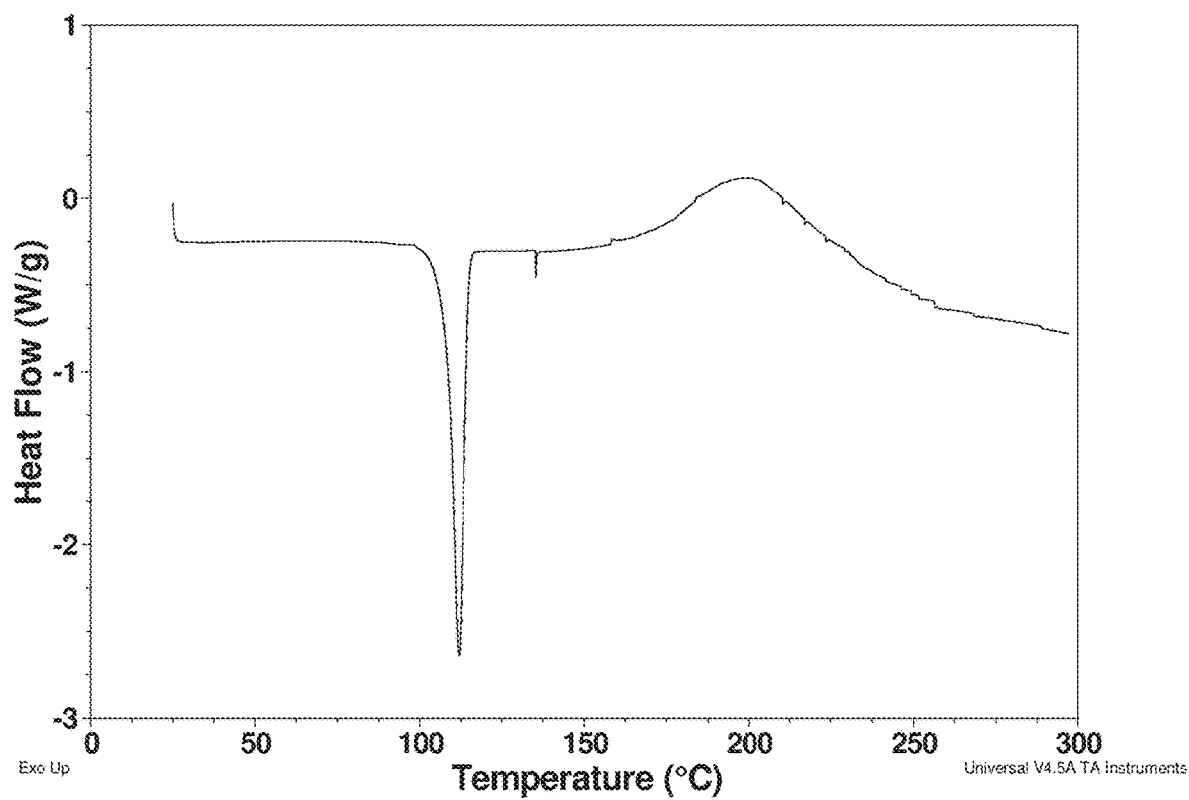
FIG. 2: DSC Thermogram of Compound A, Form A.

Differential Scanning calorimetry (DSC) analysis of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one Form A showed a melting endotherm with an onset of 106.4° C. and a peak at 111.2° C. A trace of the DSC is shown in FIG. 2.

Example 1.1: Preparation of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal, Form A Approximately 3 g of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one Form A was added to a round bottom flask containing 10 mL of methanol. A separate solution containing 1 molar equivalent (1.18 g) of 6-hydroxy-2-naphthoic acid in 5 mL methanol was then added dropwise to the round bottom flask, and the reaction was stirred overnight at room temperature. The material was filtered the following day and washed with methanol (5 mL). The recovered solid was air dried and then transferred to a vacuum oven where it was further dried overnight at 50° C. (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal was obtained as an off white solid. This form was determined to be crystalline by XRPD.

Figure 3:
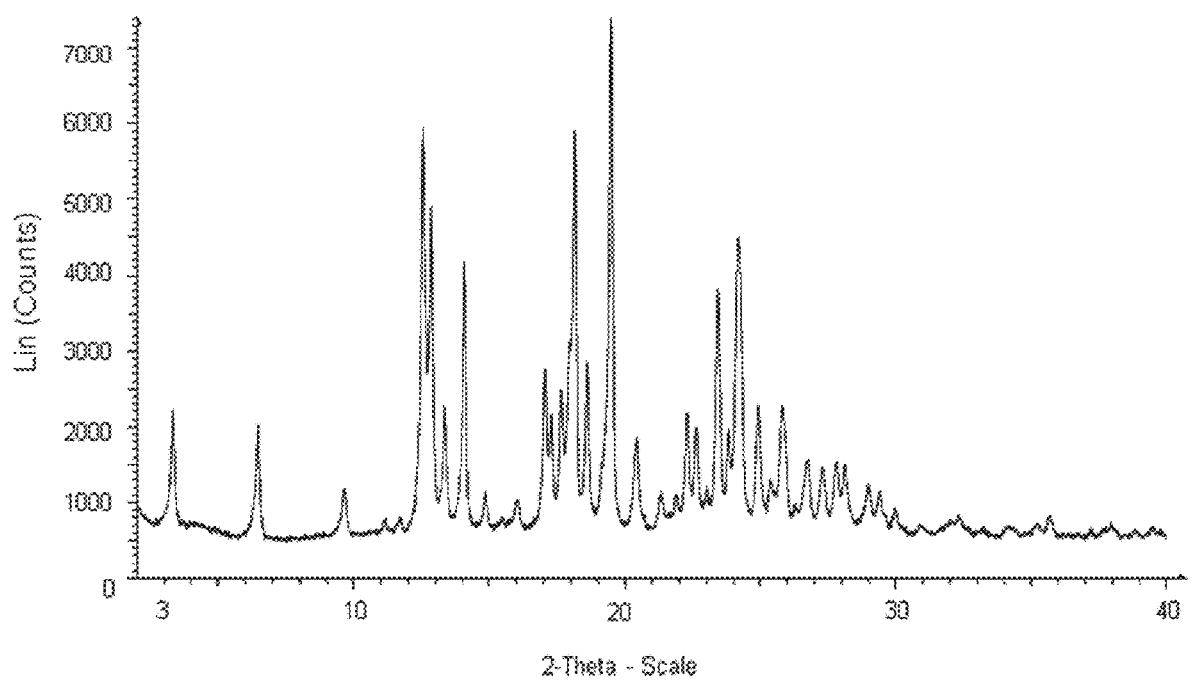
FIG. 3: X-Ray Powder Diffraction Pattern of Compound A:6-hydroxy-2-naphthoic acid (1:1) co-crystal, Form A.

This material was analysed by XRPD and DSC. XRPD of a sample of the material gave rise to a diffraction pattern as shown in FIG. 3. (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form A is characterised by at least one peak at a 2θ value of 19.5° or 12.5°, measured using CuKα radiation. The ten most prominent peaks of the XRPD are shown in Table B.

TABLE B

Ten most Prominent XRPD peaks for (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form A

| Angle 2-Theta (2θ) | Intensity % |
|---|---|
| 19.5 | 100 |
| 12.5 | 80.4 |
| 18.1 | 79.8 |
| 12.8 | 66.4 |
| 24.2 | 60.9 |
| 14.1 | 56.5 |
| 23.4 | 51.8 |
| 17.9 | 40.2 |
| 18.6 | 38.6 |
| 17.0 | 37.3 | wherein the 2-theta values are +/−0.2°.

Figure 4:
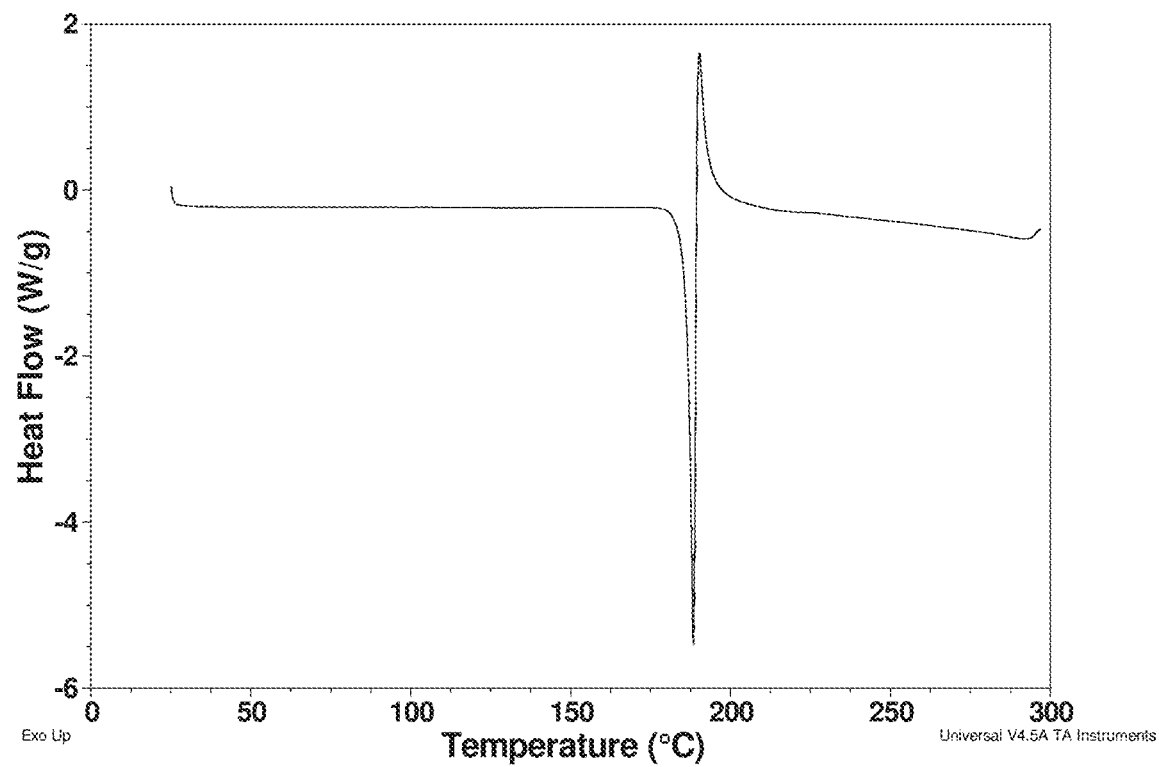
FIG. 4: DSC Thermogram of Compound A:6-hydroxy-2-naphthoic acid (1:1) co-crystal, Form A.

Differential Scanning calorimetry (DSC) analysis of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1)co-crystal Form A showed a melting endotherm with an onset of 186.3° C. and a peak at 188.3° C. A trace of the DSC is shown in FIG. 4.

Co-crystals can be defined in terms of the ΔpKa, i.e. (pKa(base)−pKa(acid)). If ΔpKa is <1, the API:coformer molecule complex is classified as a co-crystal. (Regulatory Classification of Pharmaceutical Co-Crystals, US FDA Guidance, April 2013). The pKa for the basic centre on the piperazinone in Compound A was determined to be 4.8 and the pKa for the co-former molecule 6-hydroxy-2-naphthoic acid 4.3, which gives a ΔpKa is <1 and, therefore is consistent with the formation of a co-crystal.

Figure 6:
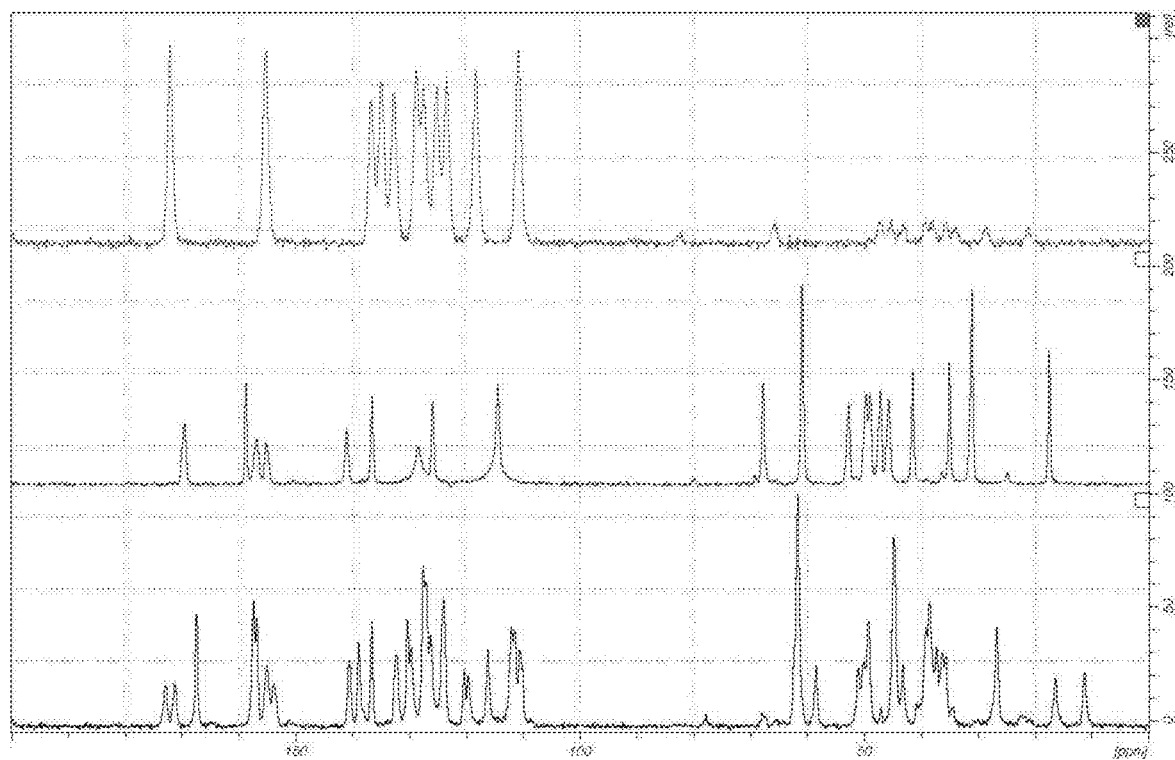
FIG. 6: $^{13}C$ cross polarisation magic angle spinning solid state NMR spectra of 6-hydroxy-2-naphthoic acid (top), Compound A free base (middle), Compound A:6-hydroxy-2-naphthoic acid (1:1) co-crystal, Form A (bottom).

$^{13}$C cross polarisation magic angle spinning solid state NMR analysis was carried out on the final product of Example 1.1, (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one and the 6-hydroxy-2-naphthoic acid co-former. The spectra are shown in FIG. 6. The bottom spectra in FIG. 6 (i.e. of the product of Example 1.1) was not sum of the spectra of the (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one (middle spectra) and the co-former (top spectra). In the top spectra there was a peak at about 172 ppm, attributed to the fully protonated carboxylic acid in the co-former. (If the carboxylic acid in the co-former is not protonated, then a peak would be expected at 177 ppm rather than 172 ppm). In the middle spectra there was a peak at about 169 ppm attributed to the carbonyl in (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one. In the spectra for the product of Example 1.1, there were 3 peaks in the carbonyl region which are not consistent with the peaks in the top or middle spectra. Furthermore, in this spectra, there was no peak at 177 ppm. Such a peak would be expected to be present if the co-former carboxylic acid is not protonated and would be indicative that a proton had transferred between the co-former and free base and a salt formed. The absence of this peak is consistent with formation of a co-crystal.

Figure 7:
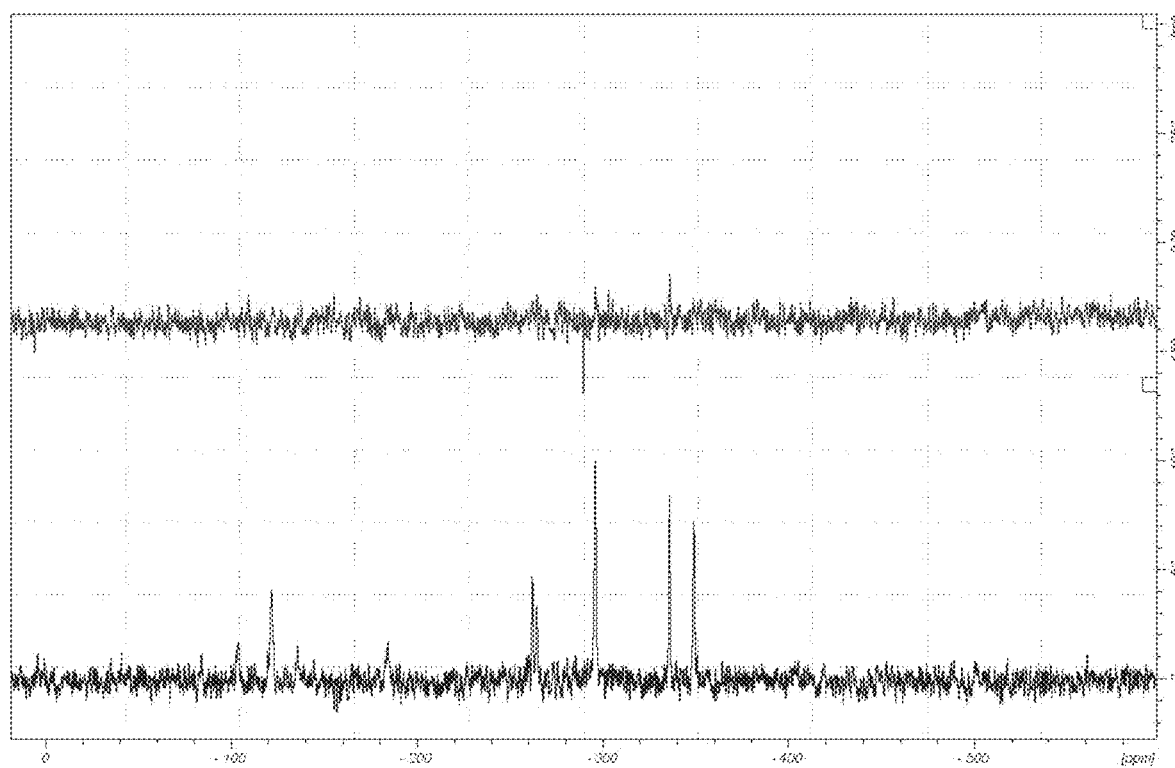
FIG. 7: $^{15}N$ cross polarisation magic angle spinning solid state NMR spectra of Compound A:6-hydroxy-2-naphthoic acid (1:1) co-crystal, Form A recorded at contact times of 2 ms (bottom) and 200 μs (top).

$^{15}$N cross polarisation magic angle spinning solid state NMR analysis was carried out on the final product of Example 1.1. Spectra were recorded at contact times of 2 ms and 200 μs and are shown in FIG. 7. The spectrum recorded with the longer contact time was consistent with at least 8 different nitrogen environments in the co-crystal whereas at the shorter contact time no peaks are observed. This was consistent with none of the nitrogen atoms exhibiting a strong dipolar coupling to a proton as would be the case if a proton had fully transferred between the conformer and the base as would be observed for a salt.

Figure 8:
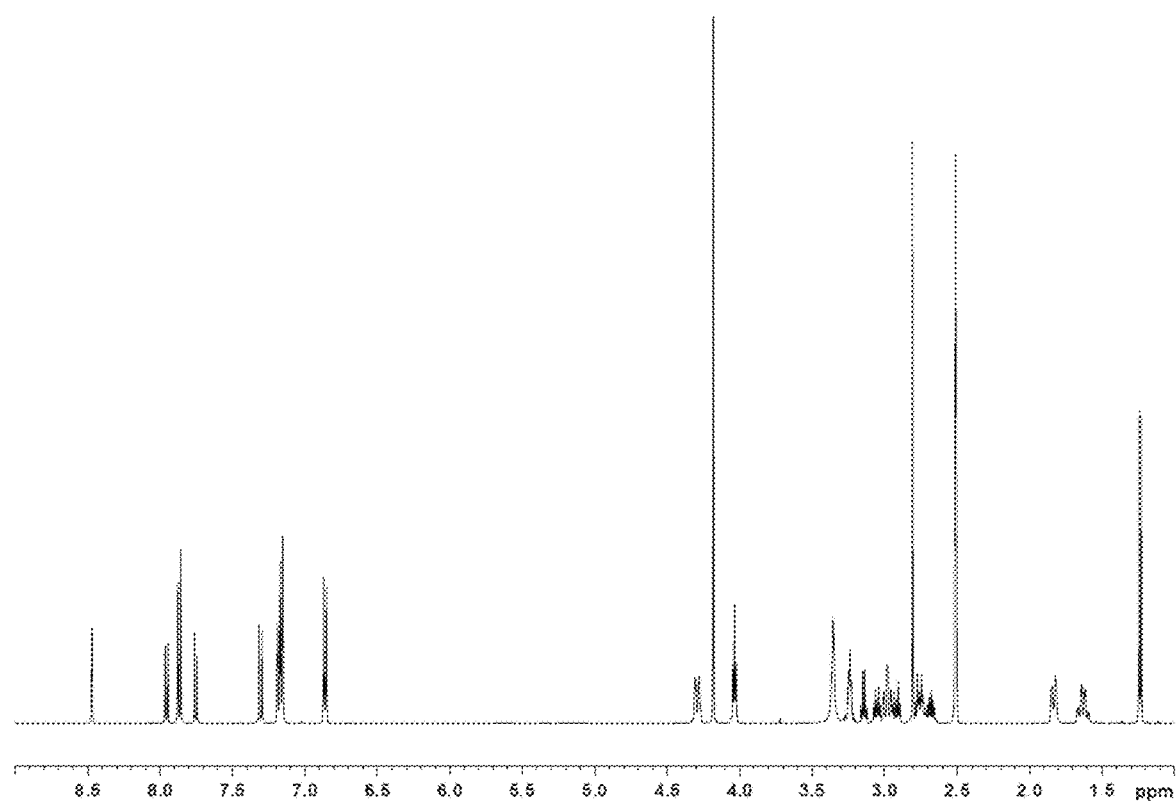
FIG. 8: ¹H NMR spectrum of Compound A:6 hydroxy-2-naphthoic acid (1:1) co-crystal, Form A.

The stoichiometry of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid co-crystal was determined by proton NMR. The material gave rise to a NMR spectrum as shown in FIG. 8. Stoichiometry was determined by integration of resonance due to (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one, for instance using the resonance at 6.85 ppm (2H) and comparison to a resonance due to 6-hydroxy-2-naphthoic acid, for instance using the resonance at 8.46 (1H), and determining the ratio between the peaks, allowing for the number of protons giving rise to the resonance signal. Stoichiometry (molar ratio) was determined to be 1:1.

$^1$H NMR (500 MHz, DMSO, 27° C.) 1.22 (3H, d), 1.62 (2H, qd), 1.82 (2H, d), 2.63-2.79 (3H, m), 2.81 (3H, s), 2.85-3.09 (4H, m), 3.13 (1H, q), 3.20-3.28 (2H, m), 4.03 (2H, t), 4.17 (3H, s), 4.28 (2H, d), 6.85 (2H, d), 7.12-7.21 (4H, m), 7.29 (1H, d), 7.75 (1H, d), 7.83-7.89 (2H, m), 7.96 (1H, d), 8.47 (1H, s), 10.15 (1H, bs), 12.81 (1H, bs)

Thus, the $^1$H NMR, $^{13}$C and $^{15}$N solid state NMR and the ΔpKa, referred to above, were consistent with the formation of Compound A:6-hydroxy-2-naphthoic acid (1:1) co-crystal Example 1.2 Preparation of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form A 4-(1-(3-methoxy-[1,2,4]triazolo[4,3-b]pyridazin-6-yl)piperidin-4-yl)phenol (0.818 kg, 2.34 mol) was mixed with ADDP (1.19 kg, 4.67 mol) and DCM (9.8 L, 150 mol) and stirred at about 10° C. Tributyl phosphine (0.98 kg, 47.6 mol) was added portionwise to the reaction mixture over 30 minutes and then it was stirred for 30 minutes. A solution of (R)-4-(2-hydroxyethyl)-1,3-dimethylpiperazin-2-one (0.503 kg, 2.80 mol) in DCM (1.64 L, 25.6 mol was then added dropwise and the reaction mixture was stirred for 24 hours.

The reaction mixture was then filtered by washing with DCM to remove the ADDP by-product. The filtrate was stirred with aqueous hydrochloric acid and the lower organic layer discarded. The aqueous layer was further washed with DCM and the lower organic layer discarded. The aqueous solution was then basified with Na$_2$CO$_3$ to pH 9-10 and extracted with DCM. The DCM layer was further washed with water and evaporated and azeotroped with methanol to remove residual water to afford crude material. The crude material was dissolved in methanol (7.5 L, 190 mol) and heated to 60° C. in vessel 1. 6-hydroxynaphthalene-2-carboxylic acid (0.360 kg, 1.87 mol) was dissolved in methanol (3.8 L, 94 mol) in vessel 2. 10% of the solution from vessel 2 was then added to vessel 1 dropwise over 10 minutes. The temperature of vessel 1 was maintained at approximately 60° C.

Compound A:6-hydroxy-2-napthoic acid (1:1) co-crystal seed material (1.2 g, 0.0018 mol), which can be made as described in Example 1.1, was added to vessel 1 and the temperature held at 60° C. for approximately 1 hour. The remaining contents of vessel 2 were then added to vessel 1 dropwise over approximately 16 hours. The resultant slurry was cooled to room temperature over 5 hours and then filtered and washed with methanol. The recovered solid was dried in a vacuum oven at 50° C. to afford (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one: 6-hydroxy-2-naphthoic acid (1:1) co-crystal (56.45% yield).

$^1$H NMR (500 MHz, DMSO-d6) ä ppm 1.43 (d, J=7.00 Hz, 3H) 1.54-1.69 (m, 2H) 1.80 (d, J=11.36 Hz, 2H) 2.74 (tt, J=12.06, 3.41 Hz, 1H) 2.84 (s, 3H) 2.91-3.03 (m, 2H) 3.25-3.63 (m, 6H) 3.83 (d, J=6.88 Hz, 1H) 4.10-4.34 (m, 7H) 6.89 (d, J=8.69 Hz, 2H) 7.09-7.22 (m, 4H) 7.28 (d, J=10.34 Hz, 1H) 7.72 (d, J=8.72 Hz, 1H) 7.79-7.88 (m, 2H) 7.92 (d, J=8.88 Hz, 1H) 8.44 (d, J=0.63 Hz, 1H) 10.12 (br. S., 1H). m/z (ES+), [M+H]+=480.

This form was determined to be crystalline by XRPD.

Preparation of 4-(1-(3-methoxy-[1,2,4]triazolo[4,3-b]pyridazin-6-yl)piperidin-4-yl)phenol 3-Chloro-6-hydrazinylpyridazine (0.753 kg) was mixed with tetramethoxymethane (8.231 mol, 1.22 kg) in methanol (5.7 L) and stirred. The resulting mixture was then heated and stirred at 55° C. for 2 hours. After cooling to 45° C., 4-(piperidin-4-yl)phenol hydrobromide (prepared as described above) (1.000 kg, 3.874 mol) was added. DIPEA (2.03 L, 11.6 mol) was then added dropwise over a period of about 10 minutes and the reaction was further stirred. Methanol (5.1 L, 126 mol) was added and the reaction mixture was stirred for at least 48 hours at approximately 45° C. The mixture was filtered and the filtrate was washed with methanol and water. The isolated solid was dried in a vacuum oven at approximately 50° C. to afford 4-(1-(3-methoxy-[1,2,4]triazolo[4,3-b]pyridazin-6-yl)piperidin-4-yl)phenol (65% yield).

$^1$H NMR (400 MHz, DMSO, 30° C.) 1.59 (2H, qd), 1.81 (2H, d), 2.67 (1H, ddt), 2.9-3.02 (2H, m), 4.17 (3H, s), 4.23-4.31 (2H, m), 6.63-6.71 (2H, m), 7.02 (2H, dd), 7.29 (1H, d), 7.84 (1H, d), 9.14 (1H, s). m/z ES+[M+H]+ 326

(R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal was analysed by XRPD and DSC. XRPD of a sample of the material gave rise to the diffraction pattern shown in FIG. 9. (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form A is characterised by at least one peak at a 2θ value of 19.4° or 12.5°, measured using CuKα radiation. The ten most prominent peaks of the XRPD are shown in Table C.

TABLE C

Ten most Prominent XRPD peaks for (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form A

| Angle 2-Theta (2θ) | Intensity % |
| --- | --- |
| 19.4 | 100 |
| 12.5 | 79.3 |
| 12.8 | 77.4 |
| 18.1 | 75.0 |
| 24.2 | 66.8 |
| 23.4 | 55.2 |
| 14.0 | 53.2 |

TABLE C-continued

Ten most Prominent XRPD peaks for (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form A

| Angle 2-Theta (2θ) | Intensity % |
| --- | --- |
| 18.6 | 37.8 |
| 17.0 | 37.5 |
| 17.9 | 36.4 | wherein the 2-theta values are +/−0.2°.

Differential Scanning calorimetry (DSC) analysis of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1)co-crystal Form A showed a melting endotherm with an onset of 184.9° C. and a peak at 187.9° C. (FIG. 10).

Thus DSC analysis showed of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1)co-crystal Form A is a high melting solid with an onset of melting in the range of 163-186° C. and a peak in the range of 169-188° C.

Example 1.1A—Material Made in a Repeat Preparation of the Route Described in Example 1.1, Resulted in a Further Form, Form B. This Form was Determined to be Crystalline by XRPD XRPD of a sample of the material gave rise to a diffraction pattern as shown in FIG. 11. (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form B is characterised by at least one peak at a 2θ value of 15.2° or 6.1°, measured using CuKα radiation. The nine most prominent peaks of the XRPD are shown in Table D.

TABLE D

Nine most Prominent XRPD peaks for (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form B

| Angle 2-Theta (2θ) | Intensity % |
| --- | --- |
| 15.2 | 40.9 |
| 6.1 | 58.1 |
| 16.8 | 64.3 |
| 12.2 | 44.0 |
| 26.1 | 43.9 |
| 28.4 | 41.0 |
| 18.3 | 34.2 |
| 3.1 | 30.6 |
| 20.7 | 25.4 | wherein the 2-theta values are +/−0.2°.

Differential Scanning calorimetry (DSC) analysis of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1)co-crystal Form B showed a melting endotherm with an onset of 169.3° C. and a peak at 172.7° C. A trace of the DSC is shown in FIG. 12.

Example 1.3: Preparation of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) Co-Crystal, Form C A sample of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form A was analysed by hot stage XRPD using a Bruker D8 advance diffractometer. The sample was heated to 210° C. with diffractograms collected every 3° C.

The sample was then cooled to 25° C. at 10 C./min, and upon opening the sample stage at the end of the experiment material was observed to have sublimed and collected on the beam knife of the diffractometer as a white powder. This white powder was collected and analysed and shown to be a different crystal form, Form C. This form was determined to be crystalline by XRPD.

XRPD of a sample of the material gave rise to a diffraction pattern as shown in FIG. 13. (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form C is characterised by at least one peak at a 2θ value of 8.2° or 24.8°, measured using CuKα radiation. The seven most prominent peaks of the XRPD are shown in Table E.

TABLE E

Seven most Prominent XRPD peaks for (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1) co-crystal Form C

| Angle 2-Theta (2θ) | Intensity % |
| --- | --- |
| 8.2 | 100 |
| 24.8 | 90.9 |
| 18.9 | 46.4 |
| 29.0 | 32.3 |
| 14.8 | 26.3 |
| 15.5 | 22.2 |
| 16.3 | 20.7 | wherein the 2-theta values are +/−0.2°.

Differential Scanning calorimetry (DSC) analysis of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one:6-hydroxy-2-naphthoic acid (1:1)co-crystal Form C showed a melting endotherm with an onset of 156.8° C. and a peak at 160.5° C. A trace of the DSC is shown in FIG. 14.

Example 2: Preparation of 1-((3S,5R)-4-(2-(4-(1-(3-methoxy-[1,2,4]triazolo[4,3-b]pyridazin-6-yl)piperidin-4-yl)phenoxy)ethyl)-3,5-dimethylpiperazin-1-yl)ethanone

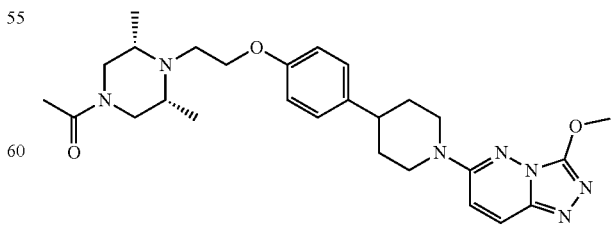

DIPEA (1.455 mL, 8.36 mmol) was added to 1-((3S,5R)-3,5-dimethyl-4-(2-(4-(piperidin-4-yl)phenoxy)ethyl)piperazin-1-yl)ethanone (1.502 g, 4.18 mmol) and 6-chloro-3-methoxy-[1,2,4]triazolo[4,3-b]pyridazine (obtained as described in Example 1, preparation of starting materials) (1.003 g, 5.43 mmol) in DMF (15 mL). The resulting solution was stirred at 80° C. for 18 hours and evaporated to dryness. The crude product was purified by ion exchange chromatography, using an SCX column. The desired product was eluted from the column using 1M NH$_3$/MeOH and evaporated to dryness to afford a brown gum. This was further purified by flash silica chromatography, elution gradient 0 to 10% 7M NH$_3$/MeOH in EtOAc. Pure fractions were evaporated to dryness to afford 1-((3S,5R)-4-(2-(4-(1-(3-methoxy-[1,2,4]triazolo[4,3-b]pyridazin-6-yl)piperidin-4-yl)phenoxy)ethyl)-3,5-dimethylpiperazin-1-yl)ethanone (0.991 g, 46.7%) as a cream foam. $^1$H NMR (400 MHz, DMSO, 100° C.) 1.06-1.1 (6H, m), 1.69 (2H, qd), 1.91 (2H, d), 1.97 (3H, s), 2.56-2.68 (4H, m), 2.78 (1H, tt), 2.99 (2H, t), 3.06 (2H, td), 3.84 (2H, br s), 4.00 (2H, t), 4.21 (3H, s), 4.27 (2H, d), 6.83-6.88 (2H, m), 7.14-7.19 (3H, m), 7.74 (1H, d). m/z: ES+[M+H]+ 508

The 1-((3S,5R)-3,5-dimethyl-4-(2-(4-(piperidin-4-yl)phenoxy)ethyl)piperazin-1-yl)ethanone used as starting material was prepared as follows:—

Preparation of benzyl 4-(4-hydroxyphenyl)piperidine-1-carboxylate

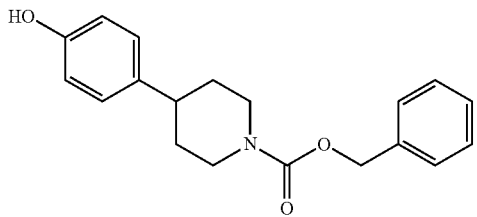 [SMILES: O=C(OCc1ccccc1)N1CCC(c2ccc(O)cc2)CC1]

Benzyl chloroformate (5.97 mL, 41.84 mmol) was added to 4-(piperidin-4-yl)phenol hydrobromide (obtained as described in Example 1, preparation of starting materials) (9 g, 34.86 mmol) and DIPEA (14.57 mL, 83.67 mmol) in DCM (150 mL). The resulting suspension was stirred for 2 hours. The reaction mixture was washed sequentially with water (2×100 mL) and 1M aqueous citric acid (100 mL). The organic layer was dried over MgSO$_4$, filtered and evaporated to afford crude product. The crude product was purified by flash silica chromatography, elution gradient 0 to 5% MeOH in DCM. Pure fractions were evaporated to dryness to afford benzyl 4-(4-hydroxyphenyl)piperidine-1-carboxylate (7.89 g, 72.7%) as a colourless gum, which solidified on standing. 1H NMR (400 MHz, DMSO, 30° C.) 1.43 (2H, qd), 1.71 (2H, d), 2.57 (1H, tt), 2.79-2.93 (2H, m), 4.11 (2H, d), 5.08 (2H, s), 6.64-6.69 (2H, m), 6.98-7.02 (2H, m), 7.28-7.33 (1H, m), 7.34-7.4 (4H, m), 9.10 (1H, s). m/z: ES+[M+H]+ 312

Preparation of benzyl 4-(4-(2-chloroethoxy)phenyl)piperidine-1-carboxylate

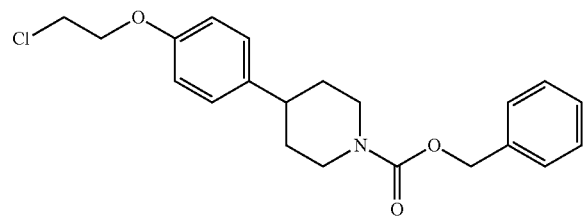 [SMILES: O=C(OCc1ccccc1)N1CCC(c2ccc(OCCCl)cc2)CC1]

1-Bromo-2-chloroethane (2.134 mL, 25.64 mmol) was added to benzyl 4-(4-hydroxyphenyl)piperidine-1-carboxylate (5.322 g, 17.09 mmol) and potassium carbonate (4.72 g, 34.18 mmol) in MeCN (80 mL). The resulting mixture was stirred at 85° C. for 18 hours. The reaction was incomplete and further potassium carbonate (4.72 g, 34.18 mmol) and 1-bromo-2-chloroethane (2.134 mL, 25.64 mmol) were added and the mixture was stirred at 85° C. for a further 48 hours. The reaction showed some progress to ~50% completion. The reaction was incomplete so the temperature was increased to 95° C. and the reaction mixture was stirred for a further 24 hours. The reaction mixture was evaporated to dryness and redissolved in EtOAc (200 mL), and washed sequentially with water (2×100 mL) and saturated brine (100 mL). The organic layer was dried over MgSO$_4$, filtered and evaporated to afford crude product. The crude product was purified by flash silica chromatography, elution gradient 0 to 5% MeOH in DCM. Pure fractions were evaporated to dryness to afford benzyl 4-(4-(2-chloroethoxy)phenyl)piperidine-1-carboxylate (3.30 g, 51.7%) as a pale yellow gum. 1H NMR (400 MHz, DMSO, 30° C.) 1.47 (2H, qd), 1.73 (2H, d), 2.64 (1H, tt), 2.81-2.95 (2H, m), 3.90 (2H, dd), 4.12 (2H, d), 4.20 (2H, dd), 5.08 (2H, s), 6.85-6.9 (2H, m), 7.12-7.17 (2H, m), 7.28-7.34 (1H, m), 7.34-7.4 (4H, m). m/z: ES+[M+H]+ 374

Preparation of benzyl 4-(4-(2-((2S,6R)-4-acetyl-2,6-dimethylpiperazin-1-yl)ethoxy)phenyl)piperidine-1-carboxylate

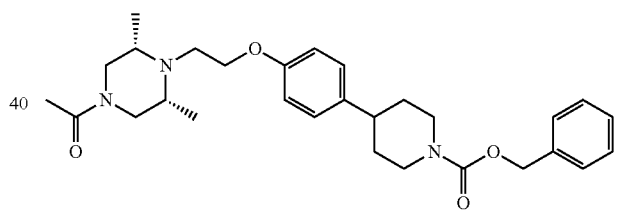

DIPEA (3.05 mL, 17.49 mmol) was added to benzyl 4-(4-(2-chloroethoxy)phenyl)piperidine-1-carboxylate (2.18 g, 5.83 mmol), 1-((3S,5R)-3,5-dimethylpiperazin-1-yl)ethanone (1.366 g, 8.75 mmol) and potassium iodide (0.968 g, 5.83 mmol) in DMA (25 mL). The resulting mixture was stirred at 125° C. for 18 hours. The reaction mixture was evaporated to dryness and redissolved in EtOAc (250 mL), and washed sequentially with water (200 mL) and saturated brine (200 mL). The organic layer was dried over MgSO$_4$, filtered and evaporated to afford crude product. This was purified by flash silica chromatography, elution gradient 0 to 4% 7M NH$_3$/MeOH in DCM. Pure fractions were evaporated to dryness to afford benzyl 4-(4-(2-((2S,6R)-4-acetyl-2,6-dimethylpiperazin-1-yl)ethoxy)phenyl)piperidine-1-carboxylate (2.180 g, 76%) as a brown gum. $^1$H NMR (400 MHz, DMSO, 100° C.) 1.06-1.1 (6H, m), 1.51 (2H, qd), 1.76-1.83 (2H, m), 1.97 (3H, s), 2.57-2.72 (5H, m), 2.93 (2H, td), 2.99 (2H, t), 3.85 (2H, br s), 4.00 (2H, t), 4.14 (2H, d), 5.12 (2H, s), 6.83-6.87 (2H, m), 7.1-7.15 (2H, m), 7.27-7.33 (1H, m), 7.34-7.38 (4H, m). m/z: ES+[M+H]+ 494

Preparation of 1-((3S,5R)-3,5-dimethyl-4-(2-(4-(piperidin-4-yl)phenoxy)ethyl) piperazin-1-yl)ethanone

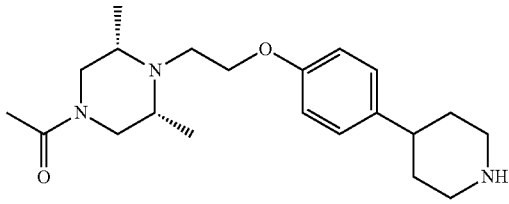 [SMILES: CC(=O)N1C[C@@H](C)N(CCOc2ccc(C3CCNCC3)cc2)[C@@H](C)C1]

Benzyl 4-(4-(2-((2S,6R)-4-acetyl-2,6-dimethylpiperazin-1-yl)ethoxy)phenyl)piperidine-1-carboxylate (2.18 g, 4.42 mmol) and 10% palladium on carbon (0.470 g, 0.44 mmol) in MeOH (45 mL) were stirred under an atmosphere of hydrogen for 5 hours. The mixture was then filtered and evaporated to dryness to give 1-((3S,5R)-3,5-dimethyl-4-(2-(4-(piperidin-4-yl)phenoxy)ethyl)piperazin-1-yl)ethanone (1.502 g, 95%) as a pale yellow gum. $^1$H NMR (400 MHz, DMSO, 100° C.) 1.07-1.1 (6H, m), 1.48 (2H, qd), 1.70 (2H, d), 1.97 (3H, s), 2.5-2.66 (7H, m), 2.99 (2H, t), 3.01-3.07 (2H, m), 3.85 (2H, br s), 4.00 (2H, t), 6.82-6.86 (2H, m), 7.09-7.13 (2H, m). m/z: ES+[M+H]+ 360

The 1-((3S,5R)-3,5-dimethylpiperazin-1-yl)ethanone used as starting material was prepared as follows:—

Preparation of N-acetyl-N-(2-(trifluoromethyl)phenyl)acetamide

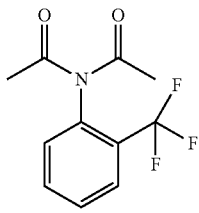 [SMILES: CC(=O)N(C(C)=O)c1ccccc1C(F)(F)F]

Acetyl chloride (132 mL, 1861.91 mmol) was added dropwise over 30 minutes to 2-(trifluoromethyl)aniline (100 g, 620.64 mmol) and pyridine (200 mL, 2482.55 mmol) in toluene (500 mL) cooled to 0° C. The reaction was heated to 50° C. and stirred for 20 hours. The mixture was then cooled to ambient temperature and washed twice with 1M aqueous citric acid (250 mL). The crude product mixture was then evaporated to half volume and treated with heptane (500 mL). The resulting slurry was stirred at 5° C. for 4 hours and then the precipitate was collected by filtration, washed with heptane (500 mL) and dried under vacuum. This gave N-acetyl-N-(2-(trifluoromethyl)phenyl)acetamide (93 g, 59.1%) as a light brown solid. $^1$H NMR (400 MHz, DMSO, 30° C.) 2.18 (6H, s), 7.58-7.93 (4H, m). m/z: ES+[M+H]+ 246

Preparation of 1-((3R,5S)-3,5-dimethylpiperazin-1-yl)ethanone

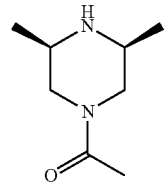

N-acetyl-N-(2-(trifluoromethyl)phenyl)acetamide (13.28 g, 52.54 mmol) was added to 2R,6S-2,6-dimethylpiperazine (5 g, 43.79 mmol) in EtOH (75 mL) and the mixture was stirred at ambient temperature for 24 hours. This was then evaporated to dryness, redissolved in DCM (25 mL) and washed with 2M aqueous HCl (25 mL). The aqueous solution was then basified to pH 14 with concentrated aqueous NaOH and extracted with DCM (2×25 mL). The combined organics were evaporated to dryness to give a yellow liquid. This was purified by flash silica chromatography, elution gradient 0 to 10% 7M NH$_3$/MeOH in DCM. Pure fractions were evaporated to dryness to afford 1-((3S,5R)-3,5-dimethylpiperazin-1-yl)ethanone (4.00 g, 66.7%) as a pale tan oil. $^1$H NMR (400 MHz, DMSO, 100° C.) 0.98 (6H, d), 1.78 (1H, br s), 1.96 (3H, s), 2.26 (2H, br s), 2.58-2.68 (2H, m), 3.94 (2H, br s).

Example 3: Preparation of (R)-4-(3-(4-(1-(3-methoxy-[1,2,4]triazolo[4,3-b]pyridazin-6-yl)piperidin-4-yl)phenoxy)propyl)-1,3-dimethylpiperazin-2-one

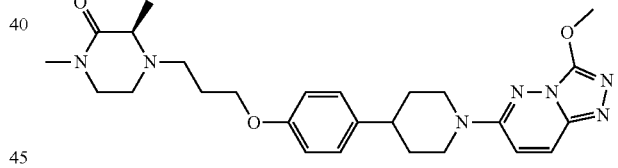

Triethylamine (0.396 mL, 2.84 mmol) was added to 6-chloro-3-methoxy-[1,2,4]triazolo[4,3-b]pyridazine (obtained as described in Example 1, preparation of starting materials) (350 mg, 1.90 mmol) and (R)-1,3-dimethyl-4-(3-(4-(piperidin-4-yl)phenoxy)propyl)piperazin-2-one (655 mg, 1.90 mmol) in DMF (10 mL) and the mixture was heated to 56° C. for 5 hours. The crude product solution was purified by ion exchange chromatography, using an SCX column. The desired product was eluted from the column using 7M NH$_3$/MeOH and evaporated to dryness to give a brown gum. This was further purified by flash silica chromatography, elution gradient 0 to 10% MeOH in DCM. Pure fractions were evaporated to dryness to afford (R)-4-(3-(4-(1-(3-methoxy-[1,2,4]triazolo[4,3-b]pyridazin-6-yl)piperidin-4-yl)phenoxy)propyl)-1,3-dimethylpiperazin-2-one (140 mg, 14.96%) as a brown foam. $^1$H NMR (400 MHz, DMSO, 30° C.); 1.20 (3H, d), 1.64 (2H, m), 1.86 (4H, m), 2.45 (2H, m), 2.72 (2H, m), 2.82 (3H, s), 3.00 (4H, m), 3.25 (2H, m), 3.98 (2H, tr), 4.19 (3H, s), 4.30 (2H, m), 6.87 (2H, dd), 7.17 (2H, dd), 7.30 (1H, d), 7.86 (1H, d). m/z ES+[M+H]+=494

The (R)-1,3-dimethyl-4-(3-(4-(piperidin-4-yl)phenoxy)propyl)piperazin-2-one used as starting material was prepared as follows:—

Preparation of tert-butyl 4-(4-hydroxyphenyl)piperidine-1-carboxylate

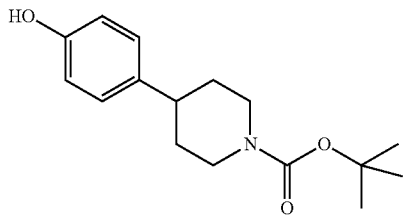 [SMILES: CC(C)(C)OC(=O)N1CCC(c2ccc(O)cc2)CC1]

Triethylamine (23.76 mL, 170.44 mmol) was added slowly to 4-(piperidin-4-yl)phenol hydrobromide (obtained as described in Example 1, preparation of starting materials) (40 g, 154.95 mmol) in DCM (190 mL) at 0° C. The resulting mixture was stirred for 20 minutes and then di-tert-butyl dicarbonate (35.5 g, 162.69 mmol) was added. The ice bath was removed and the reaction was stirred at ambient temperature for 2 hours. The reaction mixture was washed sequentially with water (2×200 mL) and saturated brine (200 mL). The organic layer was dried over MgSO$_4$, filtered and evaporated to afford crude product. The solid was taken up in MTBE (150 mL) and sonicated and slurried for 2 hours. The resulting solid was collected by filtration, washed with heptane (200 mL) and dried under vacuum to afford tert-butyl 4-(4-hydroxyphenyl)piperidine-1-carboxylate (36.0 g, 84%) as a creamy white solid product. $^1$H NMR (400 MHz, DMSO, 27° C.) 1.40 (9H, s), 1.44 (2H, d), 1.68 (2H, d), 2.49-2.59 (1H, m), 2.76 (2H, s), 4.03 (2H, d), 6.63-6.7 (2H, m), 6.96-7.04 (2H, m), 9.13 (1H, s). m/z [ES−] M−=276

Preparation of tert-butyl 4-(4-(3-chloropropoxy)phenyl)piperidine-1-carboxylate

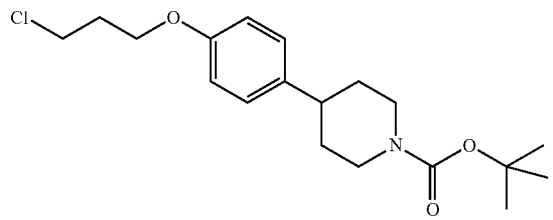 [SMILES: CC(C)(C)OC(=O)N1CCC(c2ccc(OCCCCl)cc2)CC1]

To a stirred solution of tert-butyl 4-(4-hydroxyphenyl)piperidine-1-carboxylate (9.99 g, 36.02 mmol) in MeCN (200 mL) was added 1-bromo-3-chloropropane (14.27 mL, 144.07 mmol) and potassium carbonate (19.91 g, 144.07 mmol). The reaction was stirred at 80° C. for 16 hours. The reaction mixture was diluted with water (125 mL), and extracted with DCM (200 mL). The organic layer was dried over MgSO$_4$, filtered and evaporated to afford tert-butyl 4-(4-(3-chloropropoxy)phenyl)piperidine-1-carboxylate (12.75 g, 100%) as a colourless oil. $^1$H NMR (400 MHz, CDCl$_3$, 30° C.) 1.48 (9H, s), 1.54-1.65 (2H, m), 1.79 (2H, d), 2.20 (2H, d), 2.59 (1H, tt), 2.78 (2H, t), 3.56 (2H, t), 4.02-4.13 (2H, m), 4.23 (2H, d), 6.8-6.87 (2H, d), 7.03-7.17 (2H, d).

Preparation of (R)-tert-butyl 4-(4-(3-(2,4-dimethyl-3-oxopiperazin-1-yl)propoxy) phenyl)piperidine-1-carboxylate

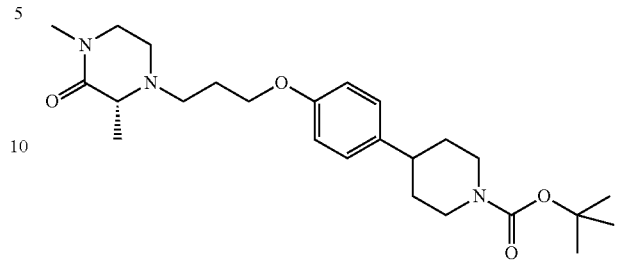

DIPEA (28.2 mL, 162.13 mmol) was added to a suspension of (R)-1,3-dimethylpiperazin-2-one hydrochloride (7.12 g, 43.23 mmol), tert-butyl 4-(4-(3-chloropropoxy)phenyl)piperidine-1-carboxylate (12.75 g, 36.03 mmol) and potassium iodide (5.98 g, 36.03 mmol) in DMA (100 mL). The solution was heated to 120° C. for 24 hours. The reaction mixture was diluted with water (200 mL) and extracted with DCM (200 mL). The organic layer was dried over MgSO$_4$, filtered and evaporated to afford crude product. This was purified by flash silica chromatography, eluting with 10% MeOH in EtOAc. Pure fractions were evaporated to dryness to afford (R)-tert-butyl 4-(4-(3-(2,4-dimethyl-3-oxopiperazin-1-yl)propoxy)phenyl)piperidine-1-carboxylate (15.50 g, 97%) as a brown oil. $^1$H NMR (400 MHz, DMSO, 30° C.) 1.19-1.22 (3H, d), 1.42 (9H, s), 1.71 (2H, d), 1.8-1.9 (2H, m), 1.96 (2H, s), 2.37-2.49 (1H, m), 2.60 (1H, ddt), 2.80 (5H, d), 2.93-3.05 (4H, m), 3.2-3.28 (2H, m), 4.05 (2H, dd), 6.8-6.9 (2H, m), 7.12 (2H, dd). m/z ES+[M+H]+=446

Preparation of 1(R)-1,3-dimethyl-4-(3-(4-(piperidin-4-yl)phenoxy)propyl)piperazin-2-one

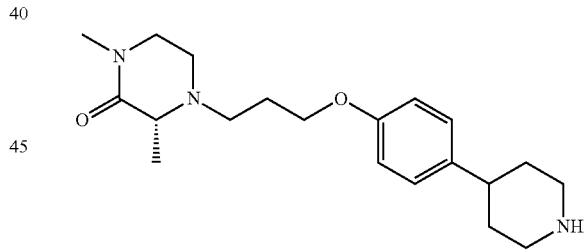

4.0M hydrogen chloride in dioxane (34.8 mL, 139.14 mmol) was added to a suspension of (R)-tert-butyl 4-(4-(3-(2,4-dimethyl-3-oxopiperazin-1-yl)propoxy)phenyl)piperidine-1-carboxylate (15.5 g, 34.78 mmol) in dioxane (20 mL). The solution was stirred to 20° C. for 2 hours. The reaction mixture was evaporated to afford crude product. The crude product was purified by ion exchange chromatography, using an SCX column. The desired product was eluted from the column using 7M NH$_3$/MeOH and pure fractions were evaporated to dryness to afford (R)-1,3-dimethyl-4-(3-(4-(piperidin-4-yl)phenoxy)propyl)piperazin-2-one (10.50 g, 87%) as a brown oil. NMR (400 MHz, DMSO, 30° C.) 1.21 (3H, d), 1.73-1.93 (6H, m), 2.4-2.46 (1H, m), 2.68-2.78 (2H, m), 2.80 (3H, s), 2.92-3.04 (4H, m), 3.18 (1H, d), 3.22-3.27 (2H, m), 3.35 (2H, s), 3.98 (2H, t), 6.89 (2H, d), 7.13 (2H, d), 8.79 (1H, bs). m/z ES+[M+H]+=346

Example 4: Preparation of 1-((3R,5S)-4-(3-(4-(1-(3-methoxy-[1,2,4]triazolo[4,3-b]pyridazin-6-yl)piperidin-4-yl)phenoxy)propyl)-3,5-dimethylpiperazin-1-yl)ethanone

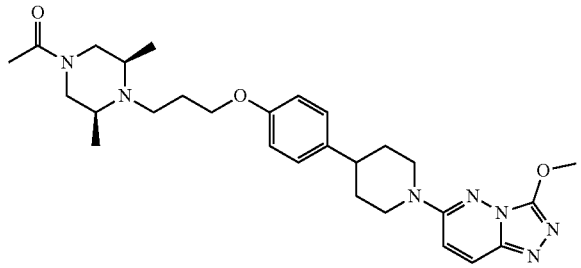 [SMILES: COc1nnc2ccc(N3CCC(c4ccc(OCCCN5[C@H](C)CN(C(C)=O)C[C@@H]5C)cc4)CC3)nn12]

Tributylphosphine (1.441 mL, 5.84 mmol) was added dropwise to 4-(1-(3-methoxy-[1,2,4]triazolo[4,3-b]pyridazin-6-yl)piperidin-4-yl)phenol (obtained as described in Example 1, preparation of starting materials) (0.95 g, 2.92 mmol), 1-((3R,5S)-4-(3-hydroxypropyl)-3,5-dimethylpiperazin-1-yl)ethanone (0.751 g, 3.50 mmol) and (E)-diazene-1,2-diylbis(piperidin-1-ylmethanone) (1.473 g, 5.84 mmol) in degassed DCM (20 mL) under nitrogen. The resulting mixture was stirred for 90 minutes and then filtered. The crude product solution was purified by ion exchange chromatography, using an SCX column. The desired product was eluted from the column using 1M NH$_3$/MeOH and evaporated to dryness to give a pale brown gum. This was further purified by flash silica chromatography, elution gradient 0 to 10% 7M NH$_3$/MeOH in EtOAc. Pure fractions were evaporated to dryness to afford 1-((3R,5 S)-4-(3-(4-(1-(3-methoxy-[1,2,4]triazolo[4,3-b]pyridazin-6-yl)piperidin-4-yl)phenoxy)propyl)-3,5-dimethylpiperazin-1-yl)ethanone (0.868 g, 57.0%) as a white foam. $^1$H NMR (400 MHz, DMSO, 100° C.) 1.04 (6H, d), 1.69 (2H, qd), 1.76-1.84 (2H, m), 1.88-1.94 (2H, m), 1.96 (3H, s), 2.51-2.55 (2H, m), 2.56-2.7 (2H, m), 2.74-2.82 (3H, m), 3.06 (2H, td), 3.81 (2H, br s), 3.98 (2H, t), 4.21 (3H, s), 4.27 (2H, d), 6.83-6.87 (2H, m), 7.13-7.18 (3H, m), 7.74 (1H, d). m/z: ES+[M+H]+ 522

The 1-((3R,5S)-4-(3-hydroxypropyl)-3,5-dimethylpiperazin-1-yl)ethanone used as starting material was prepared as follows:—

Preparation of 1-((3R,5S)-4-(3-hydroxypropyl)-3,5-dimethylpiperazin-1-yl)ethanone

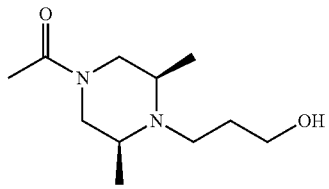

3-Bromopropan-1-ol (6.41 mL, 70.84 mmol) was added to 1-((3R,5S)-3,5-dimethylpiperazin-1-yl)ethanone (obtained as described in Example 2, preparation of starting materials) (6.51 g, 41.67 mmol) and potassium carbonate (14.40 g, 104.18 mmol) in 2-methyl tetrahydrofuran (40 mL). The resulting mixture was stirred at 80° C. for 18 hours, then filtered and evaporated to dryness. The crude product was purified by flash silica chromatography, elution gradient 0 to 6% 7M NH$_3$/MeOH in DCM. Pure fractions were evaporated to dryness to afford 1-((3R,5S)-4-(3-hydroxypropyl)-3,5-dimethylpiperazin-1-yl)ethanone (0.749 g, 8.39%) as a colourless oil. $^1$H NMR (400 MHz, DMSO, 30° C.) 0.96-1.03 (6H, m), 1.39-1.5 (2H, m), 1.96 (3H, s), 2.19-2.28 (1H, m), 2.28-2.36 (1H, m), 2.39-2.47 (1H, m), 2.67-2.77 (3H, m), 3.36 (2H, t), 3.60 (1H, dt), 4.12 (1H, dt), 4.36 (1H, br s).

The invention claimed is:

1. A method of treating cancer in a human in need thereof, comprising administering to the human an effective amount of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one or a pharmaceutically acceptable salt thereof, wherein the cancer is selected from ovarian cancer, multiple myeloma (MM), and diffuse large B-cell lymphoma (DLBCL).

2. The method of claim 1, wherein the cancer is ovarian cancer.

3. The method of claim 1, wherein the cancer is multiple myeloma (MM).

4. A method of treating cancer in a human in need thereof, comprising administering to the human an effective amount of a co-crystal of (R)-4-(2-(4-(1-(3-methoxy-[1,2,4]triazolo[4,3-b]pyridazin-6-yl)piperidin-4-yl)phenoxy)ethyl)-1,3-dimethylpiperazin-2-one and the co-former molecule 6-hydroxy-2-naphthoic acid, wherein the cancer is selected from ovarian cancer, multiple myeloma (MM), and diffuse large B-cell lymphoma (DLBCL).

5. The method of claim 4, wherein the cancer is ovarian cancer.

6. The method of claim 4, wherein the cancer is multiple myeloma (MM).

7. The method of claim 1, wherein the cancer is diffuse large B-cell lymphoma (DLBCL).

8. The method of claim 4, wherein the cancer is diffuse large B-cell lymphoma (DLBCL).

* * * * *